(12) United States Patent
Kriesel et al.

(10) Patent No.: US 8,377,043 B2
(45) Date of Patent: Feb. 19, 2013

(54) FLUID DELIVERY APPARATUS WITH BELLOWS RESERVOIR

(75) Inventors: Marshall S. Kriesel, St. Paul, MN (US);
Joshua W. Kriesel, San Francisco, CA (US)

(73) Assignee: BioQuiddity, Inc., San Francisco, CA (US)

( * ) Notice: Subject to any disclaimer, the term of this patent is extended or adjusted under 35 U.S.C. 154(b) by 0 days.

(21) Appl. No.: 12/930,128

(22) Filed: Dec. 29, 2010

(65) Prior Publication Data
US 2011/0098645 A1 Apr. 28, 2011

Related U.S. Application Data

(62) Division of application No. 10/855,446, filed on May 26, 2004, now abandoned.

(51) Int. Cl.
*A61K 9/22* (2006.01)

(52) U.S. Cl. ....................... 604/890.1; 604/132; 604/153

(58) Field of Classification Search .................. 604/132, 604/153, 207, 212, 216, 246, 93.01, 151, 604/236, 248, 256, 890.1
See application file for complete search history.

(56) References Cited

U.S. PATENT DOCUMENTS

| 4,265,241 | A  | * | 5/1981 | Portner et al. | ................. 604/131 |
| 6,183,441 | B1 | * | 2/2001 | Kriesel et al. | ................. 604/132 |

* cited by examiner

*Primary Examiner* — Kevin C Sirmons
*Assistant Examiner* — Kami A Bosworth
(74) *Attorney, Agent, or Firm* — James E. Brunton

(57) ABSTRACT

A compact fluid dispenser for use in controllably dispensing fluid medicaments, such as, antibiotics, analgesics, and like medicinal agents from the device reservoir which is provided in the form of a novel bellows type assembly. The fluid dispenser includes a unique stored energy mechanism which takes the form of a constant force spring member of novel design that provides the force necessary to continuously and substantially uniformly expel fluid from the device reservoir. The device also includes novel adjustable flow rate control assembly that is disposed intermediate the fluid reservoir outlet and the outlet port of the device for precisely controlling the rate of fluid flow from the outlet port toward the patient.

3 Claims, 32 Drawing Sheets

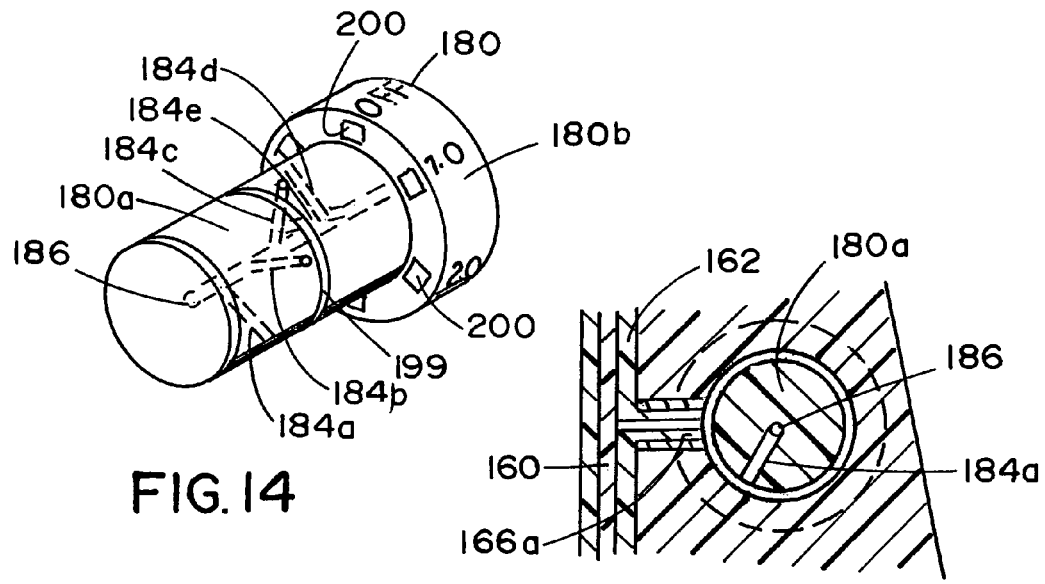
FIG. 14
FIG. 15
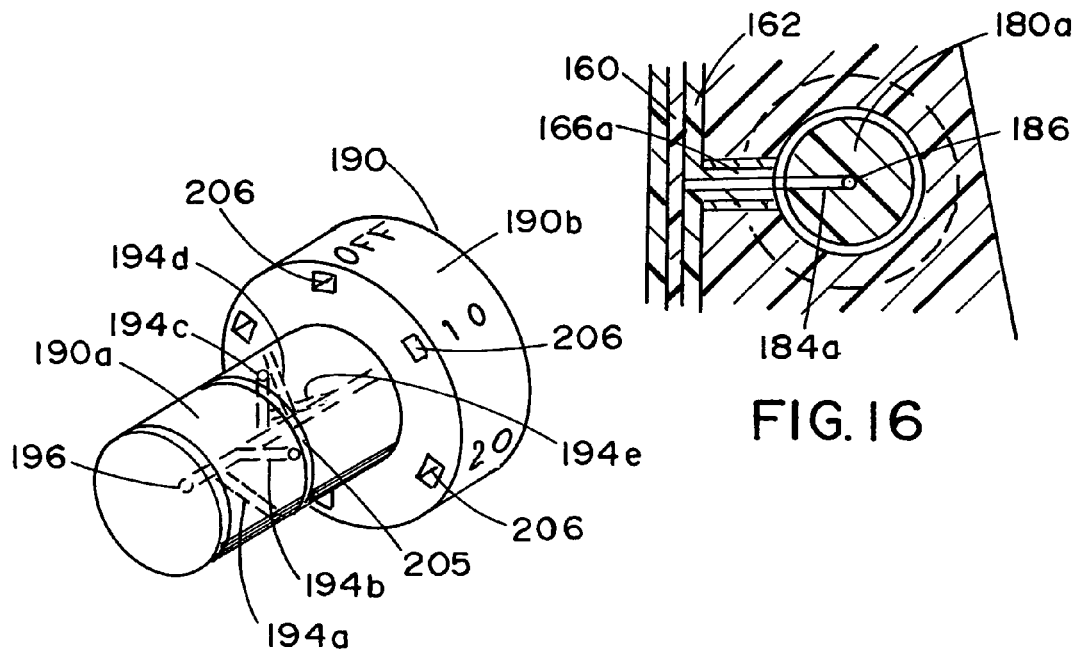
FIG. 16
FIG. 17

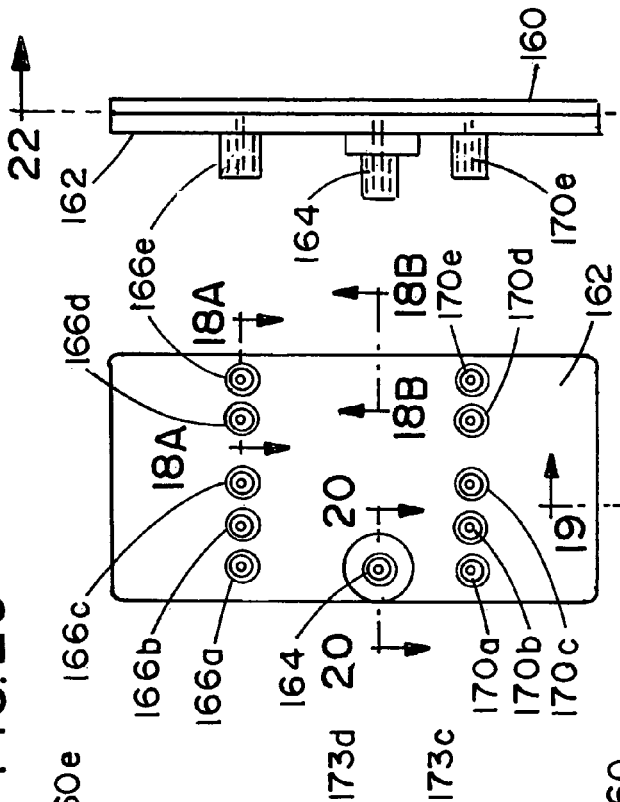

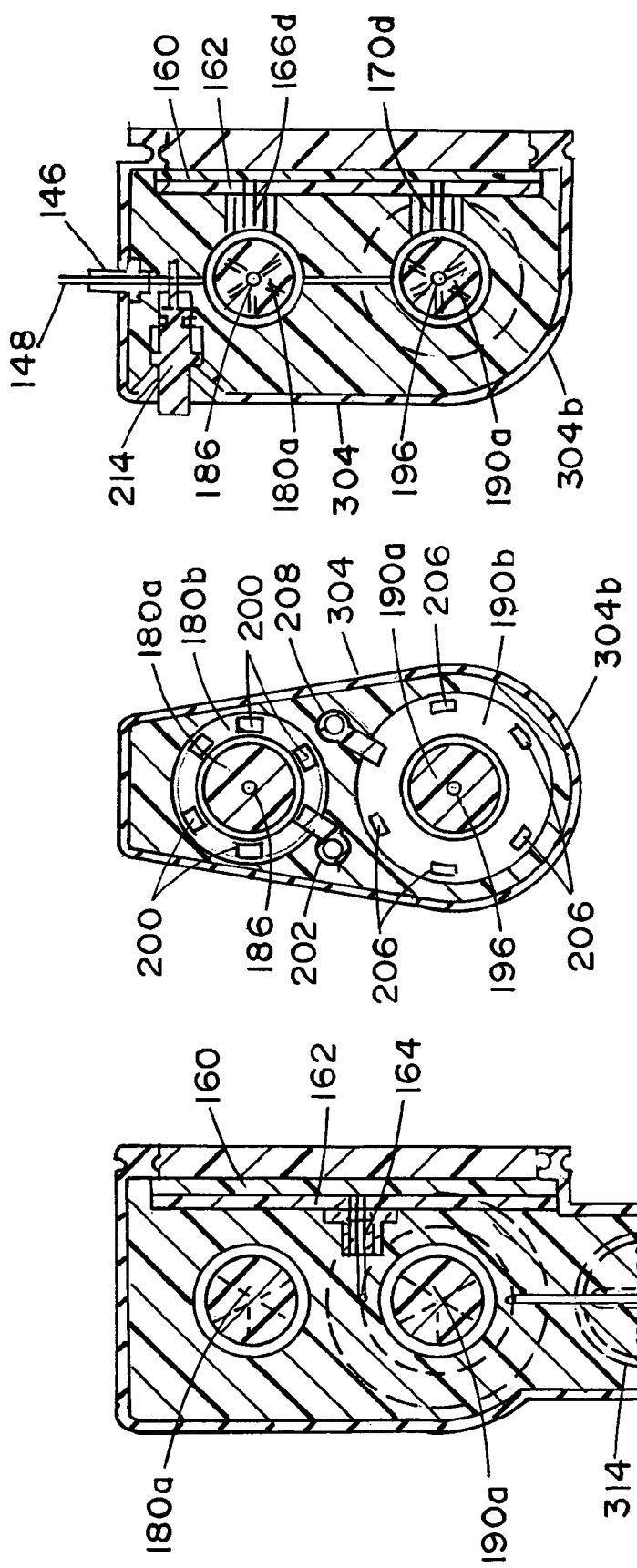

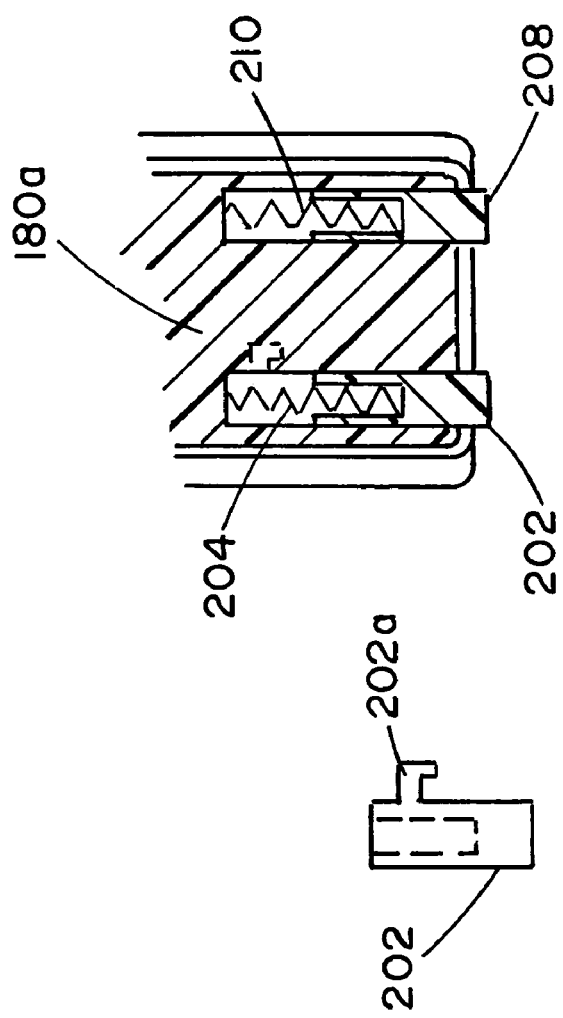
FIG. 42
FIG. 41
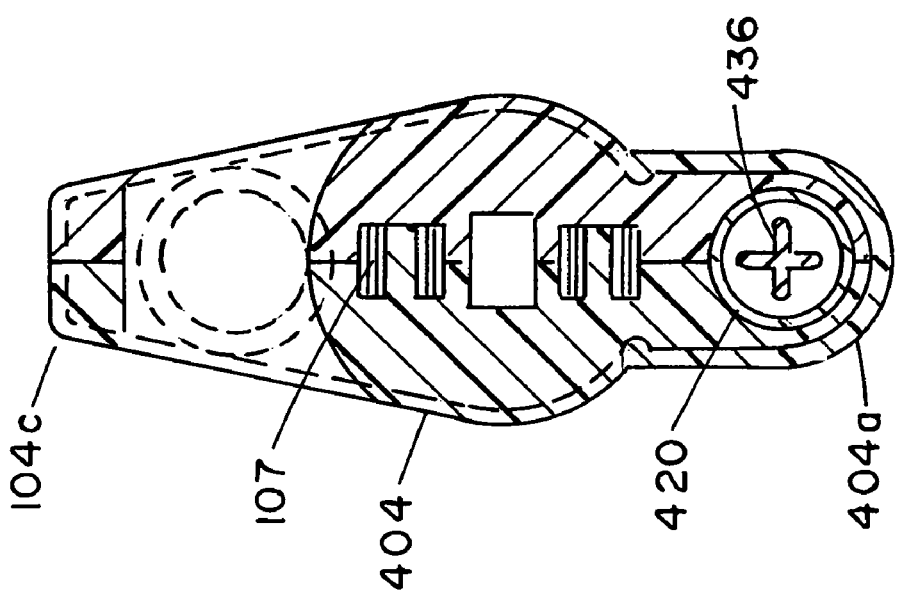
FIG. 40

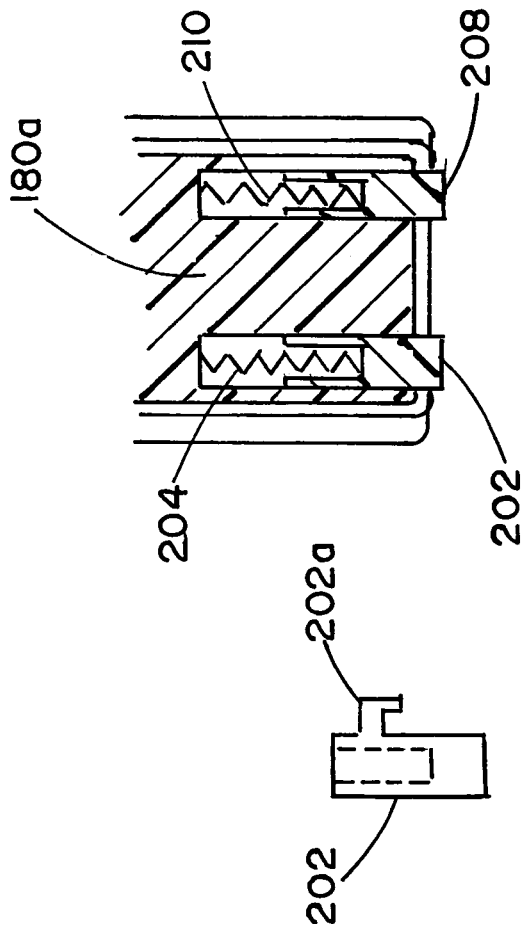
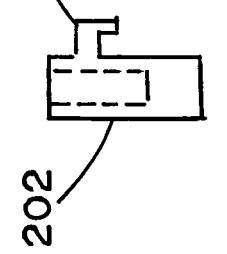
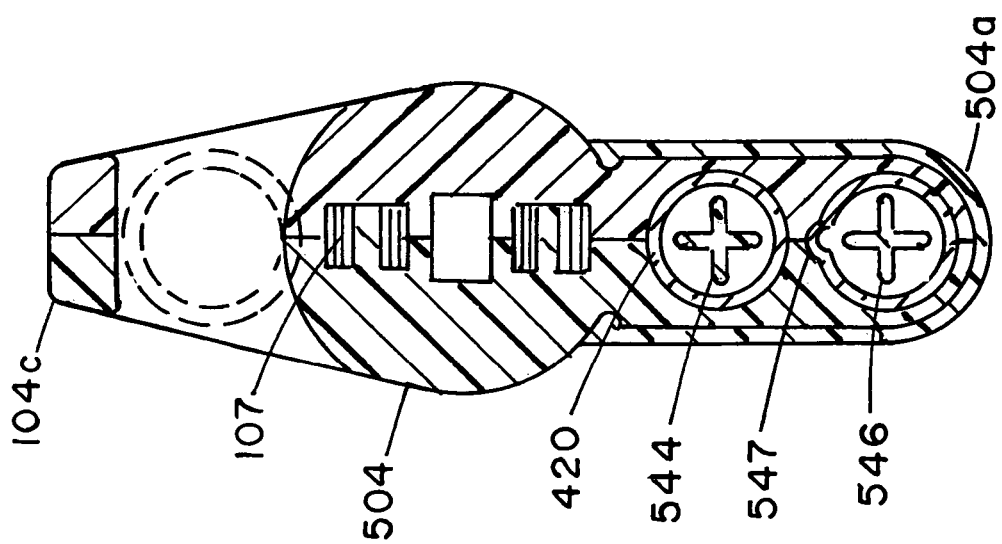

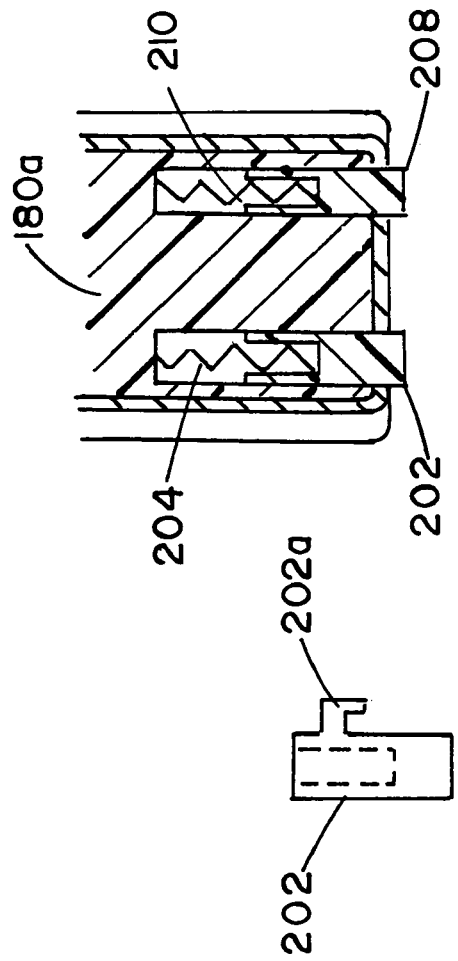
FIG. 62
FIG. 61
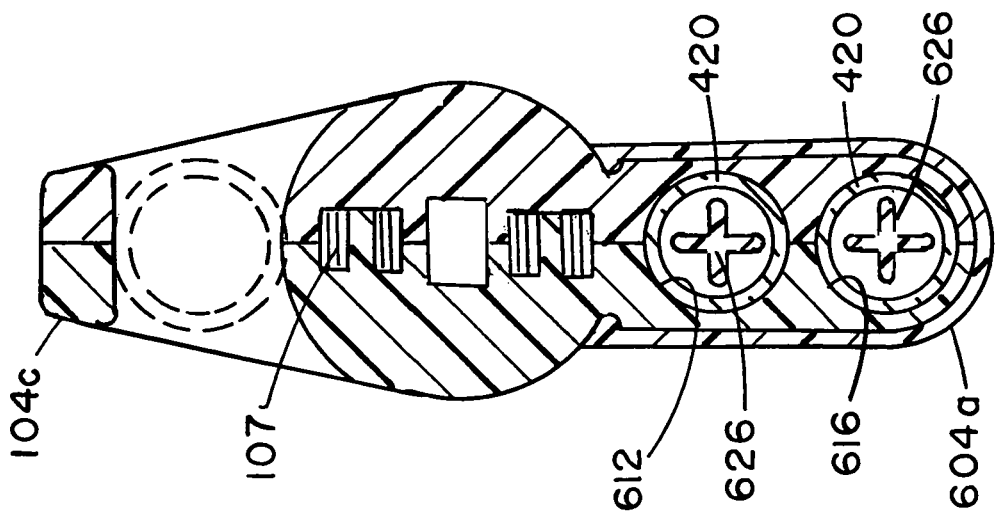
FIG. 60

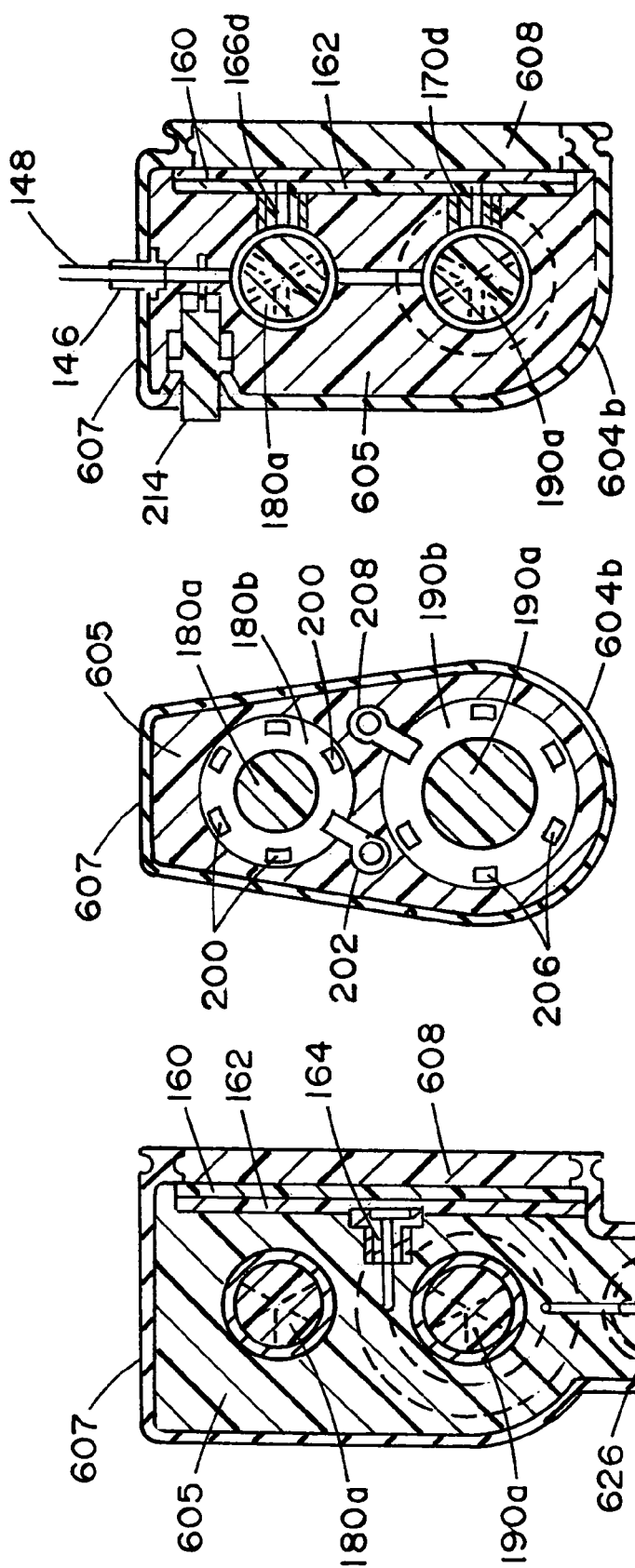

FLUID DELIVERY APPARATUS WITH BELLOWS RESERVOIR

CROSS-REFERENCE TO RELATED APPLICATIONS

This is a divisional application of application U.S. Ser. No. 10/855,446 filed May 26, 2004 now abandoned.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time, which includes a novel bellows reservoir and a unique adjustable flow rate control means for precisely adjustably controlling the rate of fluid flow from the bellows reservoir of the device toward the patient.

2. Description of Related Art Including Information Disclosed Under 37 CFR 1.97 and 1.98

Many medicinal agents require an intravenous route for administration of the medicament. The delivery device for delivering the medicament, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus. Devices from which liquid is expelled from a relatively thick-walled bladder by internal stresses within the distended bladder are well known in the prior art. Such bladder, or "balloon" type, devices are described in U.S. Pat. No. 3,469,578, issued to Bierman and in U.S. Pat. No. 4,318,400, issued to Perry.

One of the most versatile and unique fluid delivery apparatus developed in recent years is that developed by one of the present inventors and described in U.S. Pat. No. 5,205,820. The components of this novel fluid delivery apparatus generally includes: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs biopharmaceuticals, and the like from a prefilled container at a uniform rate. The dispenser, which is quite dissimilar in construction and operation from that of the present invention, includes a stored energy source in the form of a compressively deformable, polymeric elastomeric member that provides the force necessary to controllably discharge the medicament from a prefilled container, which is housed within the body of the device. After having been deformed, the polymeric, elastomeric member will return to its starting configuration in a highly predictable manner.

Another important prior art fluid delivery device is described in the U.S. Pat. No. 6,063,059 also issued to one of the present inventors. This device, while being of a completely different construction embodies a compressible-expandable stored energy source somewhat similar to that used in the apparatus of the present invention.

As will be appreciated from the discussion, which follows, the apparatus of the present invention is uniquely suited to provide precise, continuous fluid delivery management at a low cost in those cases where a variety of precise dosage schemes are of utmost importance. An important aspect of the apparatus of the present invention is the provision a novel, rotatable fluid flow rate control means that includes uniquely formed micro capillary, multichannel flow rate control channels which enable precise control of the rate of fluid flow of the medicament to the patient. More particularly, the apparatus of the present invention includes a novel, adjustable fluid flow rate mechanism which enables the fluid contained within the reservoir of the device to be precisely dispensed at various selected rates.

The apparatus of the present invention can be used with minimal professional assistance in an alternate health care environment, such as the home. By way of example, devices of the invention can be comfortably and conveniently removably affixed to the patient's body or clothing and can be used for the continuous infusion of antibiotics, such as, for example, an antibiotic sold by Abbott Laboratories under the name and style ANCIF and by Rosche under the name and style ROCEPHIN, analgesics, such as morphine and like medicinal agents.

By way of summary, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a compressible-expandable spring member that provides the force necessary to substantially, uniformly dispense various solutions from the device reservoir. Because of the simplicity of construction of the apparatus of the invention, and the straightforward nature of the energy source, the apparatus can be manufactured at low cost without in any way sacrificing accuracy and reliability.

BRIEF SUMMARY OF THE INVENTION

It is an object of the present invention to provide a compact fluid dispenser for use in controllably dispensing fluid medicaments, such as, antibiotics, analgesics, and like medicinal agents from the novel bellows-type device reservoir.

It is another object of the invention to provide a fluid dispenser of the aforementioned character, which is highly reliable and is easy-to-use by laypersons in a non-hospital environment.

Another object of the invention is to provide a small, compact fluid dispenser that includes novel fill means for filling the bellows type dispenser reservoir with the medicament to be dispensed.

Another object of the invention is to provide an apparatus which can be factory pre-filled with a wide variety of medicinal fluids or one which can readily be filled in the field shortly prior to use.

Another object of the invention is to provide a dispenser in which a stored energy source is provided in the form of a constant force spring member of novel design that provides the force necessary to continuously and substantially uniformly expel fluid from the device reservoir.

Another object of the invention is to provide a device of the aforementioned character which includes novel adjustable flow rate control means disposed intermediate the fluid reservoir outlet and the outlet port of the device for precisely controlling the rate of fluid flow from the outlet port toward the patient.

Another object of the invention is to provide a dispenser that includes precise variable flow rate selection.

Another object of the invention is to provide a fluid dispenser of the class described which is compact, lightweight, is easy for ambulatory patients to use, is fully disposable, and is extremely accurate so as to enable the infusion of precise doses of medicament over prescribed periods of time.

Another object of the invention is to provide a device of the character described which embodies a novel fluid volume indicator that provides a readily discernible visual indication of the volume of fluid remaining in the device reservoir.

Another object of the invention is to provide a self-contained medicament dispenser which is of very simple construction and yet extremely reliable in use.

Another object of the invention is to provide a fluid dispenser as described in the preceding paragraphs, which is easy and inexpensive to manufacture in large quantities.

BRIEF DESCRIPTION OF SEVERAL VIEWS OF THE DRAWINGS

FIG. 14 is a generally perspective view of the micro rate selector knob assembly of the device.

FIG. 15 is a fragmentary cross-sectional view of a portion of the flow rate control means of the invention showing the micro rate selector knob assembly in an off condition.

FIG. 16 is a fragmentary cross-sectional view of a portion of the flow rate control means of the invention showing the micro rate selector knob assembly in a delivery condition.

FIG. 17 is a generally perspective view of the macro rate selector knob assembly of the fluid dispensing device.

FIG. 18 is a side elevational view of the outer face of the cover member of the rate control assembly of the invention.

FIG. 18A is an enlarged cross-sectional view taken along lines 18A-18A of FIG. 18.

FIG. 18B is an enlarged cross-sectional view taken along lines 18B-18B of FIG. 18.

FIG. 19 is an enlarged cross sectional view taken along lines 19-19 of FIG. 18.

FIG. 20 is an enlarged cross sectional view taken along lines 20-20 of FIG. 18.

FIG. 21 is an end view of the flow rate control assembly of this latest form of the fluid delivery device of the invention.

FIG. 22 is a view taken along lines 22-22 of FIG. 21.

FIG. 23 is an end view of the inner face of the base member of the rate control assembly of this latest form of the invention.

FIG. 24 is an enlarged, fragmentary view of the portion identified in FIG. 23 as "24".

FIG. 33 is a cross-sectional view taken along lines 33-33 of FIG. 27.

FIG. 34 is a cross-sectional view taken along lines 34-34 of FIG. 27.

FIG. 35 is a cross-sectional view taken along lines 35-35 of FIG. 27.

FIG. 40 is a cross-sectional view taken along lines 40-40 of FIG. 37.

FIG. 41 is a side view of one of the locking arms of the device.

FIG. 42 is a cross-sectional view taken along lines 42-42 of FIG. 39.

FIG. 50 is a cross-sectional view taken along lines 50-50 of FIG. 47.

FIG. 51 is a side view of one of the locking arms of the device.

FIG. 52 is a cross-sectional view taken along lines 52-52 of FIG. 49.

FIG. 60 is a cross-sectional view taken along lines 60-60 of FIG. 57.

FIG. 61 is a side view of one of the locking arms of the device.

FIG. 62 is a cross-sectional view taken along lines 62-62 of FIG. 59.

FIG. 63 is a cross-sectional view taken along lines 63-63 of FIG. 57.

FIG. 64 is a cross-sectional view taken along lines 64-64 of FIG. 57.

FIG. 65 is a cross-sectional view taken along lines 65-65 of FIG. 57.

DETAILED DESCRIPTION OF THE INVENTION

Figure 1:
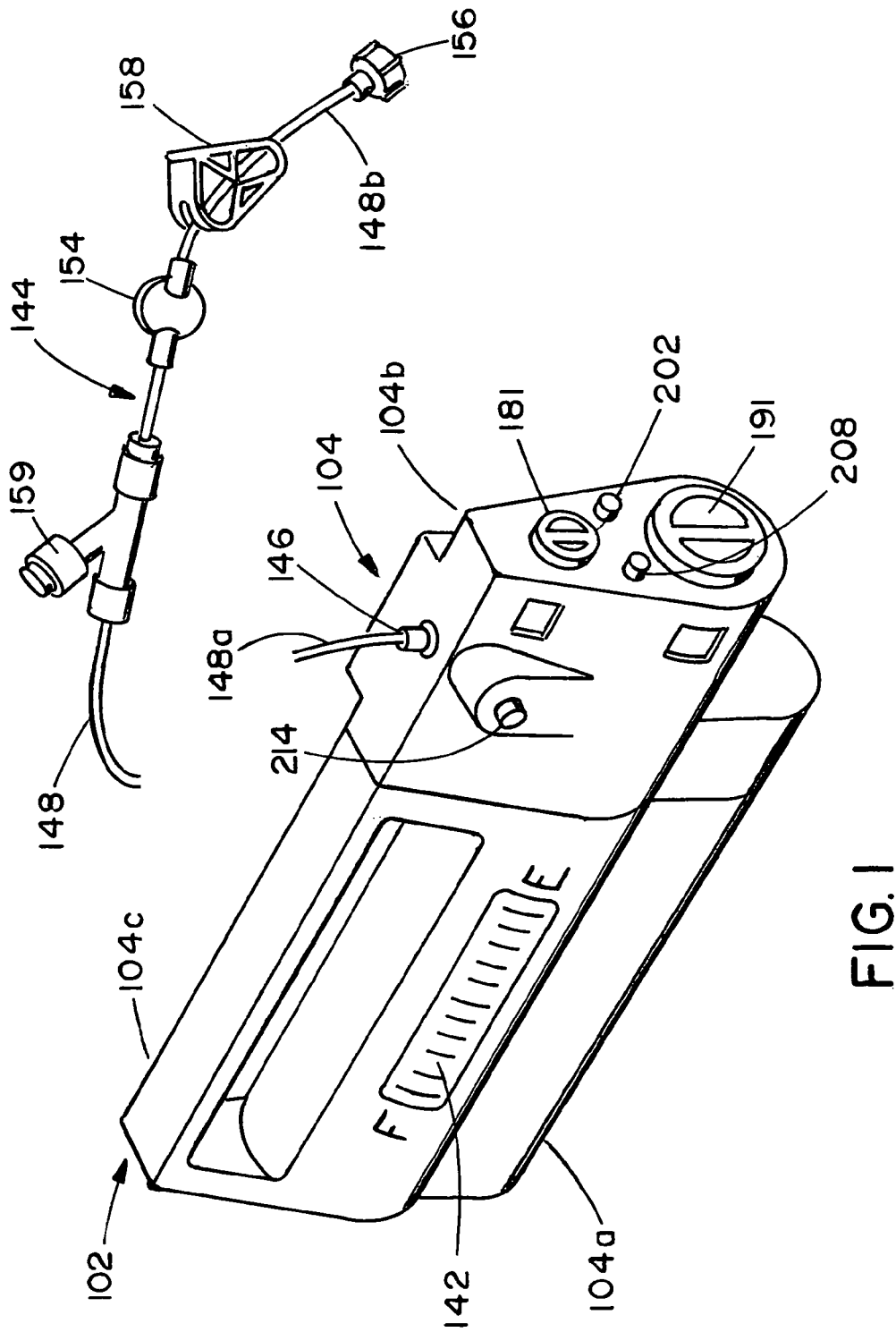
FIG. 1 is a generally perspective view of one form of the fluid dispensing device of the present invention showing one side of the device.
Figure 2:
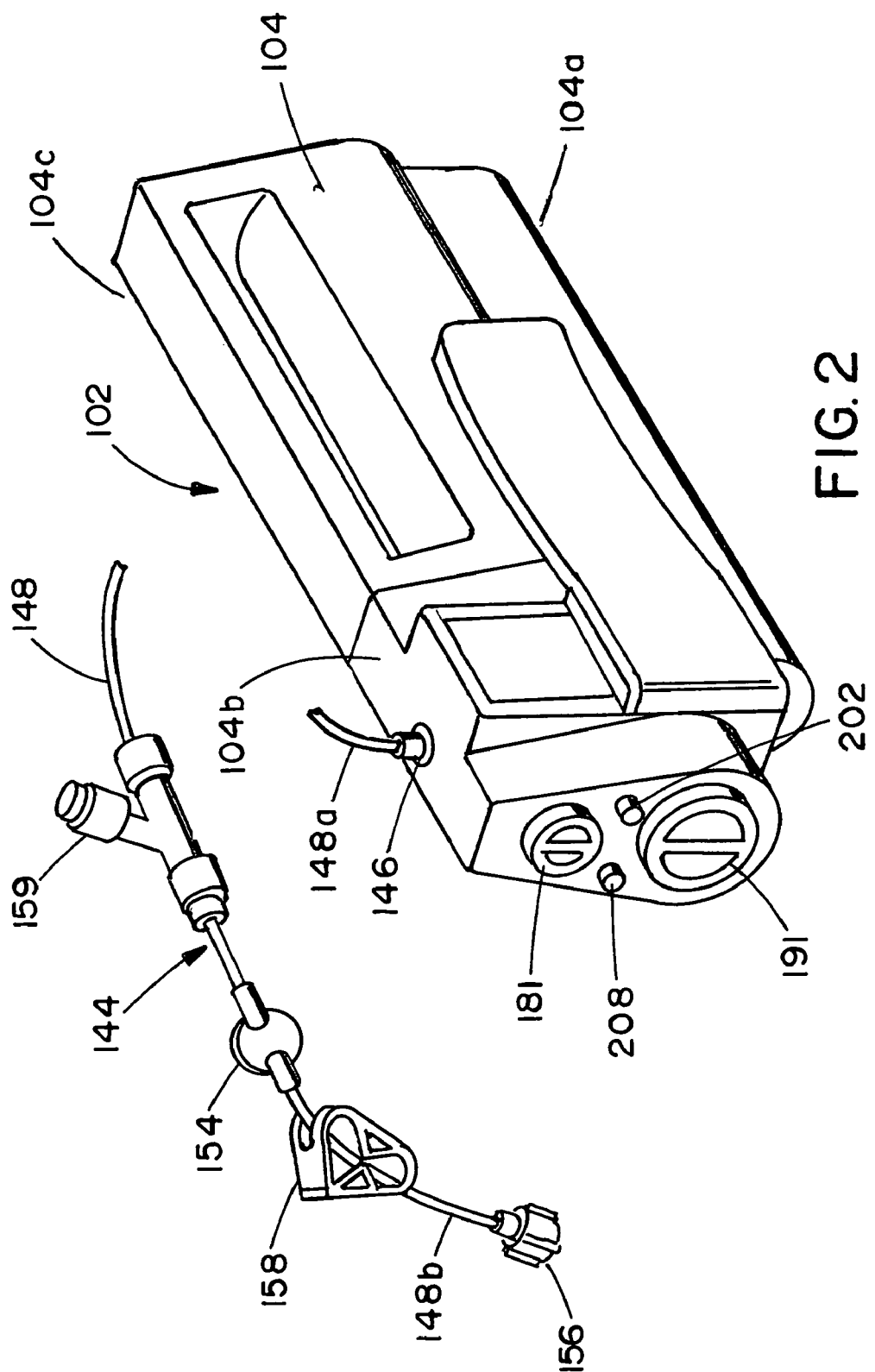
FIG. 2 is a generally perspective view of the fluid dispensing device shown in FIG. 1 showing the opposite side of the device.

Referring to the drawings and particularly to FIGS. 1 through 26, one form of the apparatus of the present form of the invention is there illustrated and generally designated by the numeral 102. As best seen in FIGS. 1, 2 and 13, the apparatus here comprises a snap together outer housing 104 having first and second portions 104a and 104b, respectively. Housing portion 104a comprises the reservoir portion, while housing portion 104b comprises the rate control, fill and delivery and control portions. When snapped together the housing portions define a carrying handle 104c.

Figure 7:
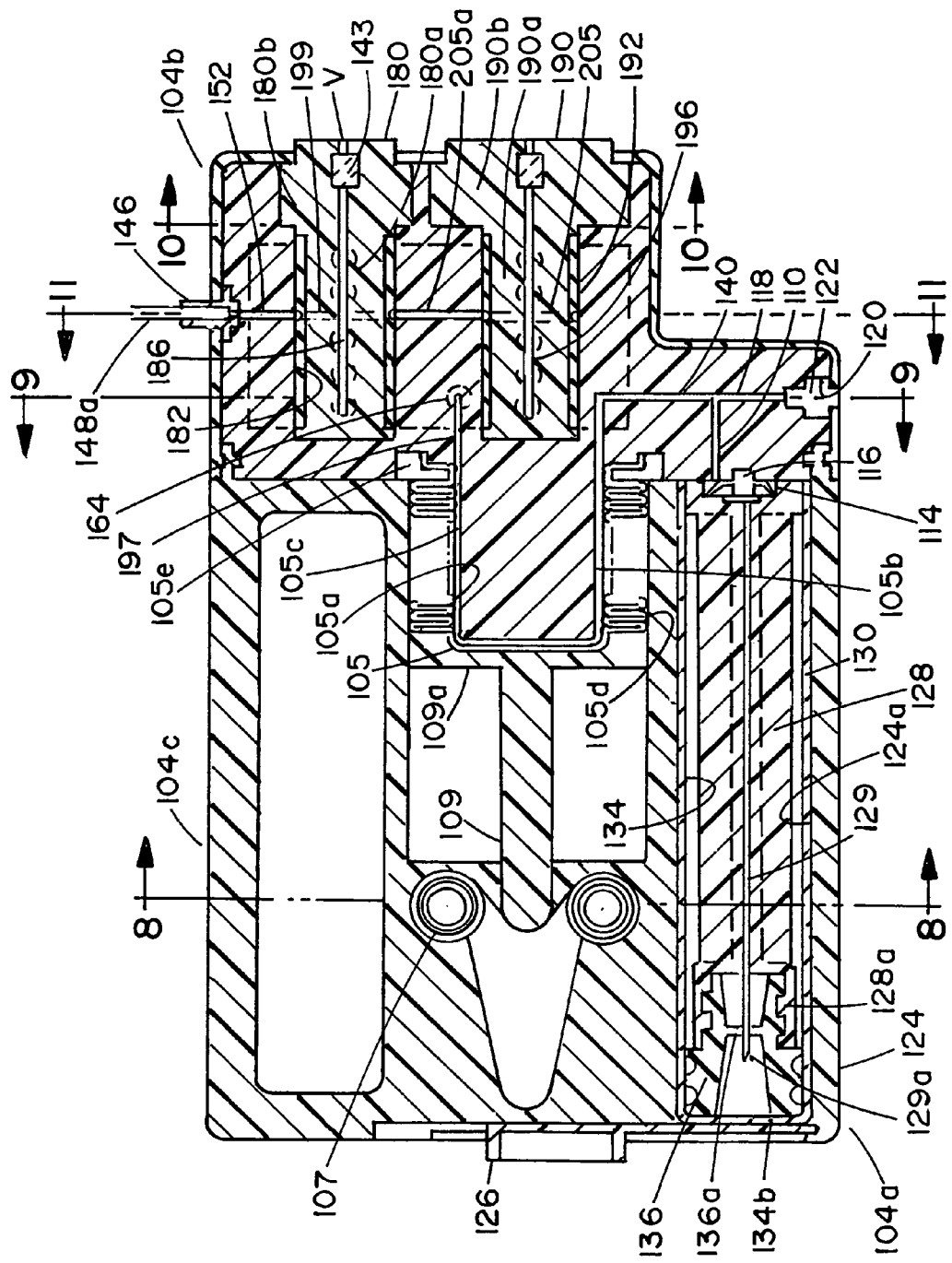
FIG. 7 is a cross-sectional view taken along lines 7-7 of FIG. 4.

Disposed within first portion 104a of outer housing 104 is a novel expandable housing 105 having a fluid reservoir 105a (FIGS. 7 and 13) provided with an inlet passageway 105b for permitting fluid flow into the fluid reservoir and an outlet 105c for permitting fluid flow from the fluid reservoir. Expandable housing 105, which can be constructed from a metal or plastic material and can include a coating of the character presently to be described, comprises a bellows structure having an expandable and compressible, accordion-like, annular-shaped sidewall 105d, the configuration of which is best seen in FIGS. 7 and 13. A capture ring 105e (FIGS. 7 and 13) secures the expandable housing in position.

Disposed within second portion 104a of outer housing 104 is the novel stored energy means of the invention for acting upon inner expandable housing 105 in a manner to cause the fluid contained within fluid reservoir 105a to controllably flow outwardly of the housing, through the dispensing means of the invention and onwardly toward the patient. In the present form of the invention, this important stored energy means comprises a constant force spring member 107 that is carried within the second portion 104a of the outer housing. Spring member 107 is first extended by fluid flowing into reservoir 105a and then controllably retracts in the manner shown in FIG. 7 to cause fluid flow from the outer housing through the dispensing means of the invention. Stored energy member or constant force spring 107, which is a special variety of extension spring, is readily commercially available from several sources including Barnes Group Inc. of Bristol, Conn., Stock Drive Products/Sterling Instrument of Hyde Park, N.Y. and Walker Corporation of Ontario, Canada. Constant force extension spring 107 is basically a high stress, long deflection device that offers great advantages when used in applications where very low or zero gradient is desired, where space is a factor and where very high reliability is required. Constant force springs, such as spring 107, provide markedly superior constant force loading when compared to conventional helical extension or like springs. Spring 107, after being expanded, tends to uniformly return toward its starting configuration and in so doing will exert an inward pressure on a pusher means, shown here as pusher member 109 of the character shown in FIG. 7. Pusher member 109 is operably coupled with the expandable housing 105 and functions to move the expandable housing from an expanded configuration to a contracted configuration. More particularly, as the spring 107 returns toward its starting configuration, it will act on pusher member 109 in a manner to move the expandable housing from an expanded configuration to a contracted configuration and in so doing will cause the fluid contained within the fluid reservoir 105a to flow outwardly through outlet 105c and toward the flow rate control means of the invention at a substantially constant rate.

Forming an important aspect of the apparatus is the fill means, which is carried by the first portion 104a of outer housing 104 and functions to controllably fill the reservoir 105a with the fluid to be dispensed. As best seen in FIG. 7, housing portion 104b includes a fluid passageway 110 that communicates with inlet 105b of fluid reservoir 105a. Fluid passageway 110 also communicates with a cavity 114 formed within first portion 104b of the housing. Disposed within cavity 114 is a conventional, umbrella type check valve 116, which permits fluid flow toward fill passageway 110, but blocks fluid flow in the opposite direction. Passageway 110 also communicates, via a passageway 118, with a cavity 120 that houses a pierceable septum 122, which comprises a part of one form of the fill means of the invention. Septum 122 may be a conventional slit septum, the character well understood by those skilled in the art, which is pierceable by the cannula of a filling syringe assembly (not shown) which contains the medicinal fluid to be dispensed and which, in a manner presently to be described, can be used to fill or partially fill reservoir 105a via passageway 110.

First portion 104a of housing 104 includes a vial receiving portion 124 that is normally closed by a closure cap 126. Connector portion 124 is provided with a chamber 124a for telescopically receiving the medicament fill vial assembly of the invention the character of which will presently be described. An elongated support 128, which is mounted within chamber 124a includes a threaded end portion 128a and carries an elongated, longitudinally extending, hollow needle 129 having a central fluid flow passageway.

Figure 12:
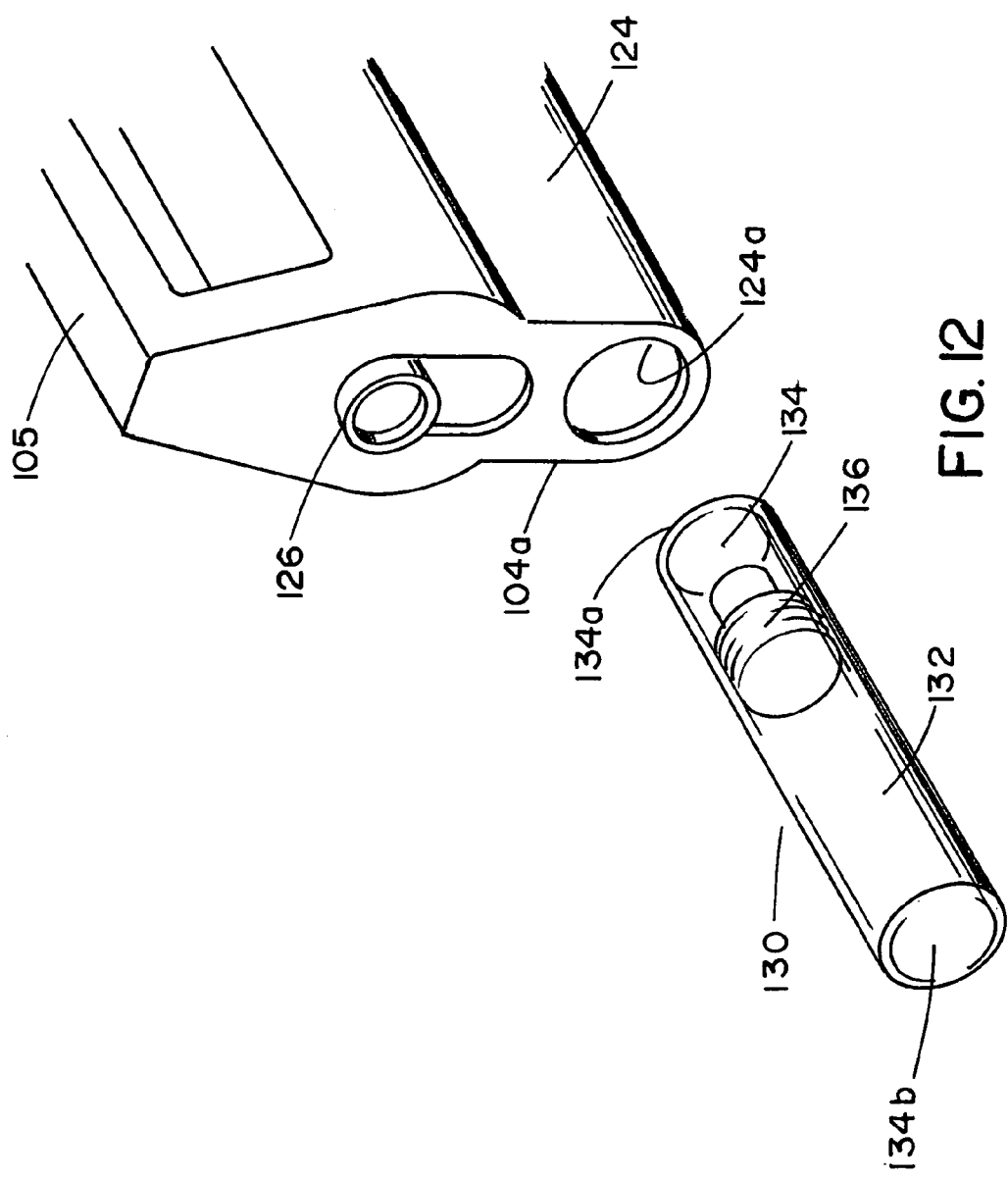
FIG. 12 is a generally perspective, exploded view of the rear portion of the fluid dispensing device shown in FIG. 1.
Figure 13:
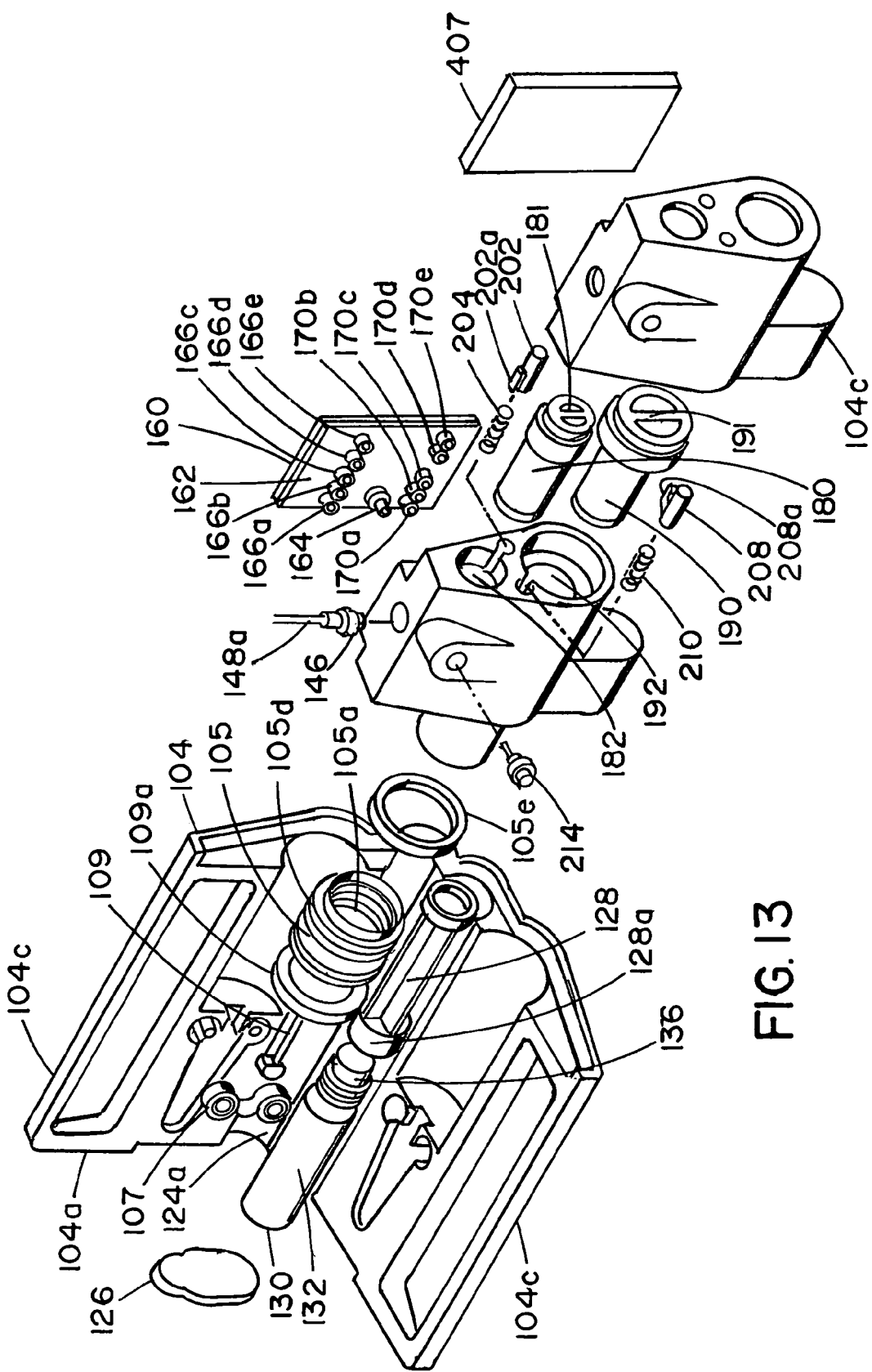
FIG. 13 is a generally perspective exploded view of the fluid dispensing device shown in FIG. 1.

Referring particularly to FIG. 12, the medicament containing fill vial assembly 130 includes a fill vial 132 having a fluid chamber 134 for containing the injectable fluid medicament. Chamber 134 is provided with a first open end 134a and second closed end 134b. First open end 134a is sealably closed by closure means here provided in the form of an externally threaded elastomeric plunger 136 which is telescopically movable within chamber 134 from a first location where the plunger is disposed proximate first open end 134a to the second, device-fill location where the plunger is disposed proximate second closed end 134b (FIG. 7).

After removal of closure cap 126 from connector portion 124, vial assembly 130 can be inserted into chamber 124a (FIGS. 7 and 13). As the fill vial assembly is so introduced and the plunger 136 is threadably interconnected with threaded end 128a of support 128, the sharp end 129a of the elongated needle 129 will pierce the central wall 136a of the elastomeric plunger in the manner shown in FIG. 7. An inward pressure exerted on the vial assembly will cause the vial to move inwardly of chamber 124a and will cause the structural support 128 to move the elastomeric plunger inwardly of the vial chamber 134 in a direction toward the second or closed end 134b of the vial chamber. As the plunger is moved inwardly of the vial, the fluid contained within the vial chamber will be expelled there from into the hollow elongated needle 129, which has pierced the central wall 136a of the elastomeric plunger. The fluid will then flow past conventional umbrella type check valve 116, into passageway 110 and thence into a passageway 140 which communicates with reservoir inlet 105b.

As the fluid flows into reservoir 105a, the bellows 105d will expand in a manner to exert a rearward pressure on the plunger end portion 109a of pusher member 109 causing it to move rearwardly. As the pusher member moves rearwardly, it will exert forces on spring member 107 causing it to expand from its retracted configuration shown in FIG. 7 to its expanded configuration. This rearward movement of pusher member 109 can be viewed through the volume indicator window 142 indicating that the reservoir has changed from an empty configuration to a filled configuration (FIG. 1).

As the reservoir 105a fills with fluid, any gases trapped within the reservoir will be vented to atmosphere via vent means "V", mounted in portion 104b of the housing. This vent means here comprises a gas vent 143 that can be constructed of a suitable hydrophobic porous material such as a porous plastic.

Upon opening the fluid delivery path to the fluid delivery means of the invention, shown here as a conventional administration set 144 (FIG. 1), the stored energy means, or spring 107, will tend to return to its starting configuration thereby controllably urging fluid flow outwardly of reservoir 105a via the flow control means of the invention the character of which will presently be described.

Administration set 144 is connected to the second portion 104b of housing 104 by a connector 146 in the manner shown in FIG. 1 of the drawings. The proximal end 148a of administration line 148 of the administration set is in communication with an outlet fluid passageway 152 which is formed in housing portion 104b in the manner best seen in FIG. 7. Disposed between the proximal end 148a and the distal end of the administration line are a conventional gas vent and filter 154. Provided at the distal end 148b, is a luer connector 156 of conventional construction (FIG. 1). Between gas vent and filter 154 and luer connector 156 is a conventional line clamp 158 and disposed between gas vent and filter 144 and the proximal end 148a of the administration line is a conventional "Y" site 159.

A number of beneficial agents can be contained within vial 132 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

As the fluid contained within reservoir 105a is urged outwardly thereof by the stored energy means, the fluid will flow under pressure through reservoir outlet 105c (FIG. 7) and then on toward the flow control means, or flow control assembly of this latest form of the invention. This important flow control means functions to precisely control the rate of fluid flow flowing from the reservoir 105a toward the patient.

Referring to FIGS. 18 through 26, it can be seen that the flow rate control means of the flow control means of this latest form of the invention comprises an assembly which includes a base plate, or rate control member 160 and a mating cover member 162 (FIG. 21). Cover member 162 is provided with a fluid inlet port 164 and a plurality of spaced apart, generally tubular shaped micro rate fluid outlet ports 166a, 166b, 166c, 166d and 166e respectively. As illustrated in FIG. 22, flow rate control member, or base plate 160 is uniquely provided with a plurality of micro rate flow control channels 160a, 160b, 160c, 160d and 160e respectively, each having an inlet and an outlet. As indicated in the drawings, the outlets of the micro rate flow control channels are in communication with the spaced apart micro rate outlet ports of the cover member 162 and the inlet port is in fluid communication with reservoir 105a. Cover member 162 is also provided with a plurality of spaced apart, generally tubular shaped macro rate fluid outlet ports 170a, 170b, 170c, 170d and 170e respectively. Flow rate control member, or base plate 160 is also uniquely provided with a plurality of macro rate flow control channels 172a, 172b, 172c, 172d and 172e respectively, each having an inlet and an outlet 173a, 173b, 173c, 173d and 173e. The outlets of the macro rate flow control channels are in communication with the spaced apart macro rate outlet ports of the cover member 162.

As indicated in FIG. 20, inlet port 164 is provided with a filter member 175 of conventional construction for filtering particulates from the fluid flowing toward the various rate control channels.

Also forming a part of the flow control means of this latest form of the invention is a micro rate selector knob 180 that is carried within a horizontal bore 182 formed in housing portion 104b. Selector knob 180 includes a body portion 180a and an enlarged diameter head portion 180b. As illustrated in FIG. 14, selector knob 180 is uniquely provided with a plurality of radially extending flow control channels 184a, 184b, 184c, 184d and 184e, each having an inlet port and an outlet port which is in fluid communication with an axially extending passageway 186. Axially extending passageway 186 is, in turn, in fluid communication with administration line 148. In a manner presently to be described, micro selector knob, which comprises a part of the selector means of this latest form of the invention, functions to selectively align one of the inlets of the radially extending flow control channels of the selector knob with a selected one of the spaced apart micro rate fluid outlets 166a, 166b, 166c, 166d and 166e of the rate control cover 162 (FIG. 18).

Also forming a part of the flow control means of this latest form of the invention is a macro rate selector knob 190 that is carried within a horizontal bore 192 formed in housing portion 104b. Selector knob 190 includes an enlarged diameter head portion 190b and a generally cylindrical body portion 190a. As illustrated in FIG. 17, selector knob 190 is uniquely provided with a plurality of radially extending flow control channels 194a, 194b, 194c, 194d and 194e, each having an inlet port and an outlet port which it is in fluid communication with an axially extending passageway 196. Axially extending passageway 196 is, in turn, in fluid communication with administration line 148.

In a manner presently to be described, selector knob 190, which also comprises a part of the selector means of this latest form of the invention, functions to selectively align one of the inlets of the radially extending flow control channels of the macro selector knob with a selected one of the spaced apart macro rate fluid outlets 170a, 170b, 170c, 170d and 170e of the rate control cover 162 (FIG. 18).

Figure 25:
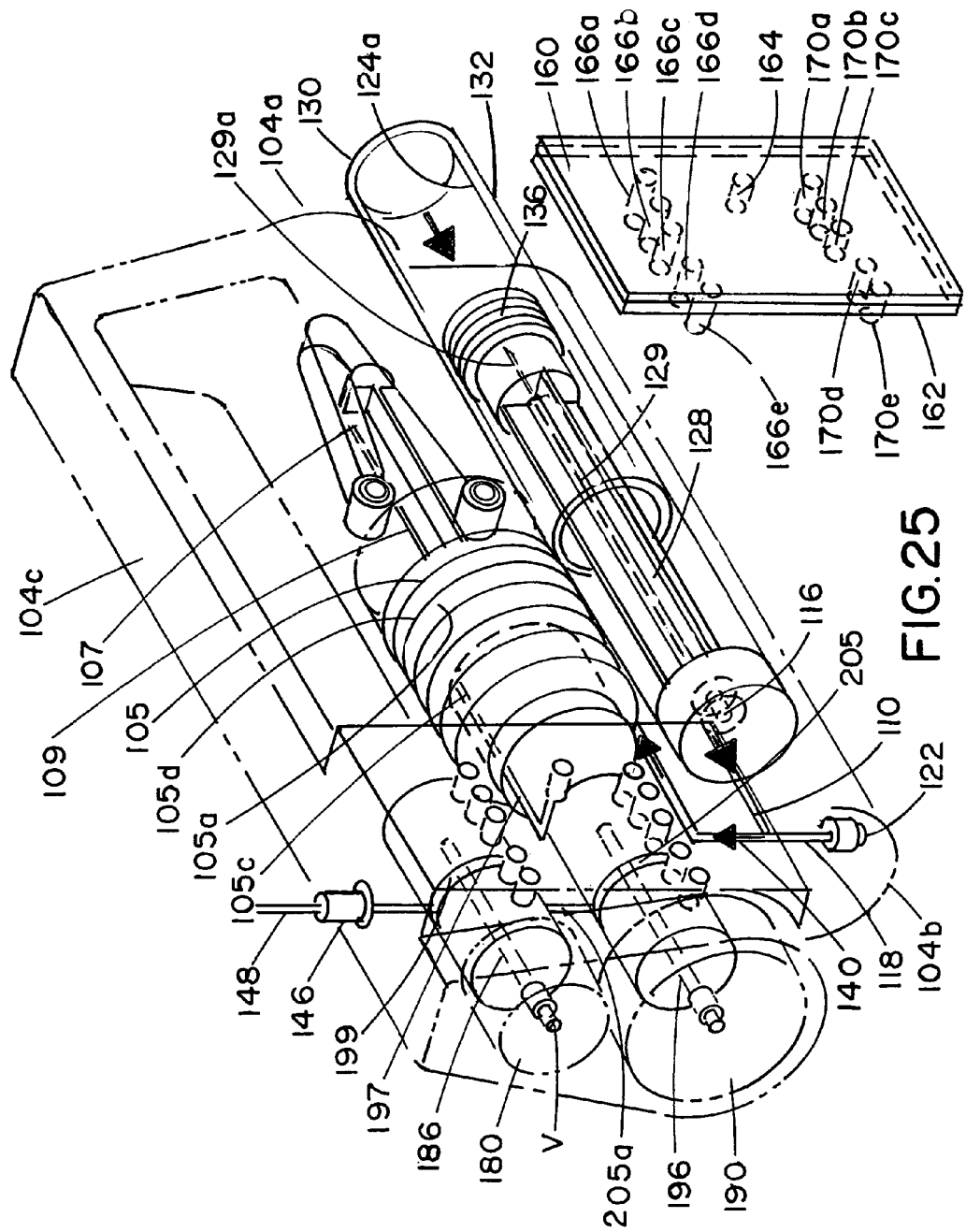
FIG. 25 is a generally perspective illustrative view of a portion of the fluid delivery device of the invention showing the fluid flow path during the fill step.
Figure 26:
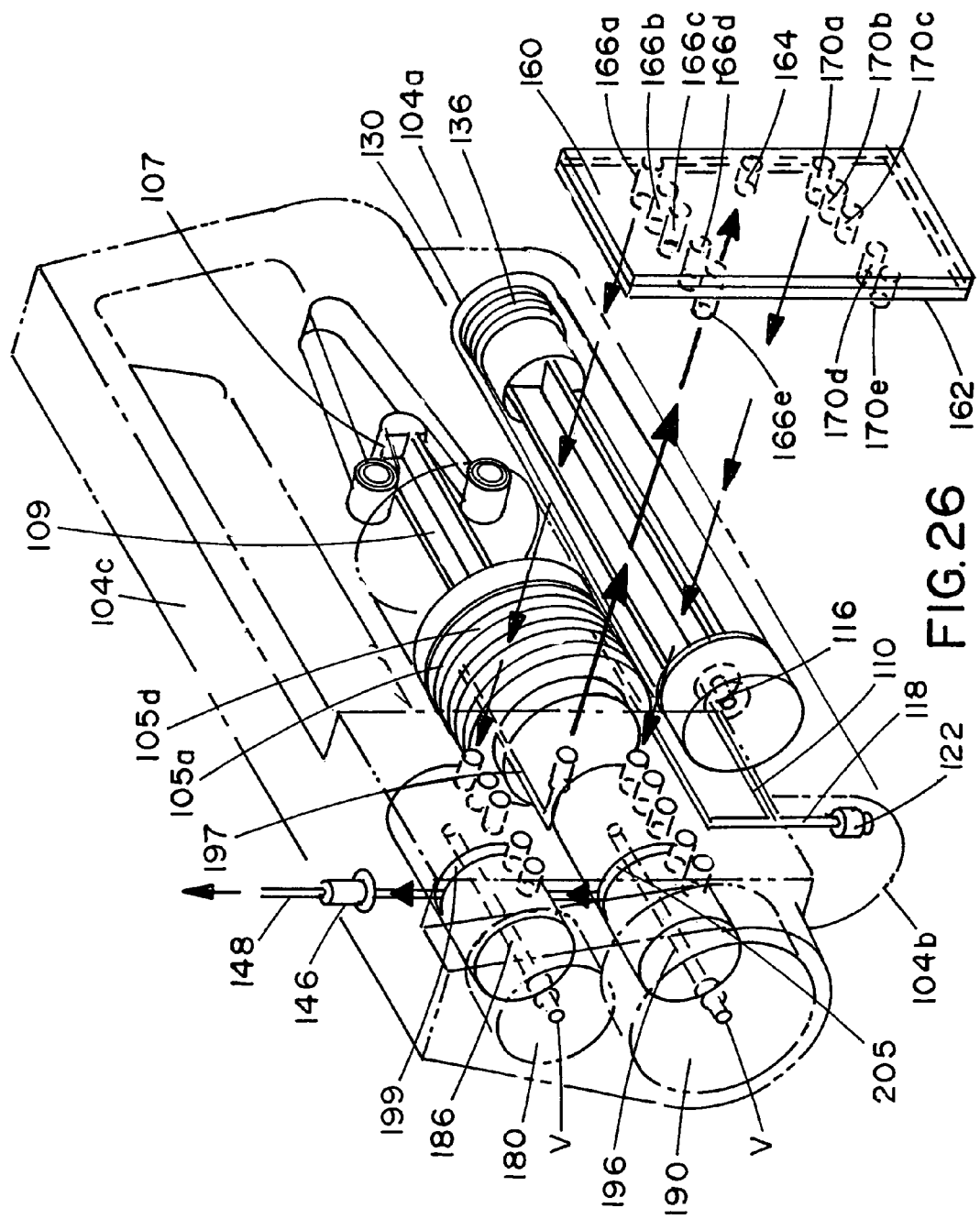
FIG. 26 is a generally perspective illustrative view of a portion of the fluid delivery device of the invention showing the fluid flow path during the fluid delivery step.

As best seen in FIGS. 7 and 25, inlet port 164 of the rate control assembly is in communication with the outlet port 105c of reservoir 105a via a passageway 197 with which it is in communication. As the pusher assembly 109 is urged forwardly by the stored energy means, the fluid contained within reservoirs 105a will flow through the outlet port 105c, through passageway 197 and into inlet 164 of the rate control assembly in a manner to permit each of the micro channels and each of the macro channels of the rate control plate 160 to fill with the medicinal fluid to be dispensed to the patient.

In using the apparatus, rotation of the micro rate selector knob 180 will permit each of the spaced outlets of the micro channels to selectively be aligned with a selected one of the outlets 166a, 166b, 166c, 166d and 166e of the rate control cover 162. The fluid can then flow into a selected one of the plurality of passages 184a, 184b, 184c, 184d and 184e, formed in the micro rate selector knob 180, into axially extending passageway 186, into the administration line 148 via a circumferentially extending fluid flow passageway 199 (see FIGS. 7 and 26), into the administration line 148 and then on to the patient at a precise micro rate of flow. To assist in rotating knob 180, the knob is provided with a finger gripping bar 181 (FIG. 1).

In operation, upon rotation of selector knob 180 a selected one of the micro channels outlets 166a, 166b, 166c, 166d and 166e will align with a selected inlet 184a, 184b, 184c, 184d and 184e of selector knob 180 (see FIGS. 15 and 16). For example, when outlet 166a is in index with inlet 184a (FIG. 16), fluid will flow from reservoir 105a through micro channel 160a, into selector knob inlet 184a via cylindrical outlet port 166a, into central passageway 186, into annular passageway 199, into passageway 152, into the administration line 148 and toward that patient at a precise, predetermined first rate. Similarly, when outlet 166c of micro channel 160c is aligned with inlet 184c of selector 180, fluid will flow from reservoir 105a through micro channel 160c, into selector inlet 184c via cylindrical outlet port 166c, into central passageway 186, into annular passageway 199, into passageway 152, into the administration line 148 and toward the patient at a second rate.

Figure 6:
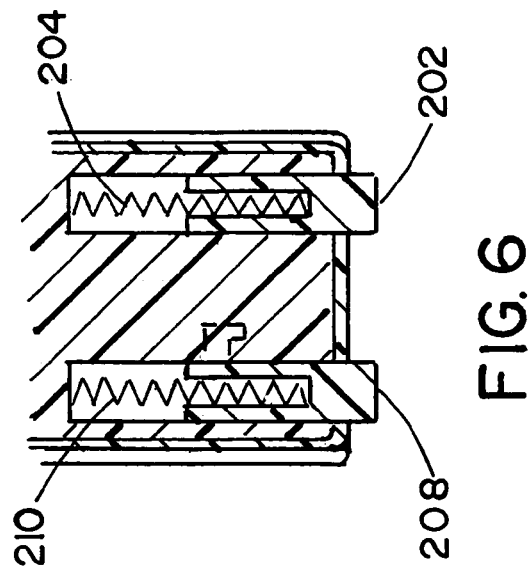
FIG. 6 is a cross-sectional view taken along lines 6-6 of FIG. 4.
Figure 5:
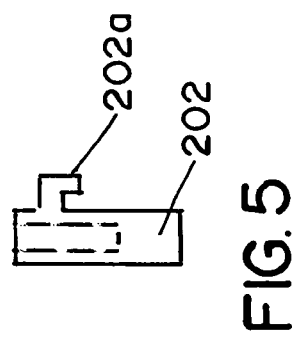
FIG. 5 is a side view of one of the locking arms of the device.
Figure 8:
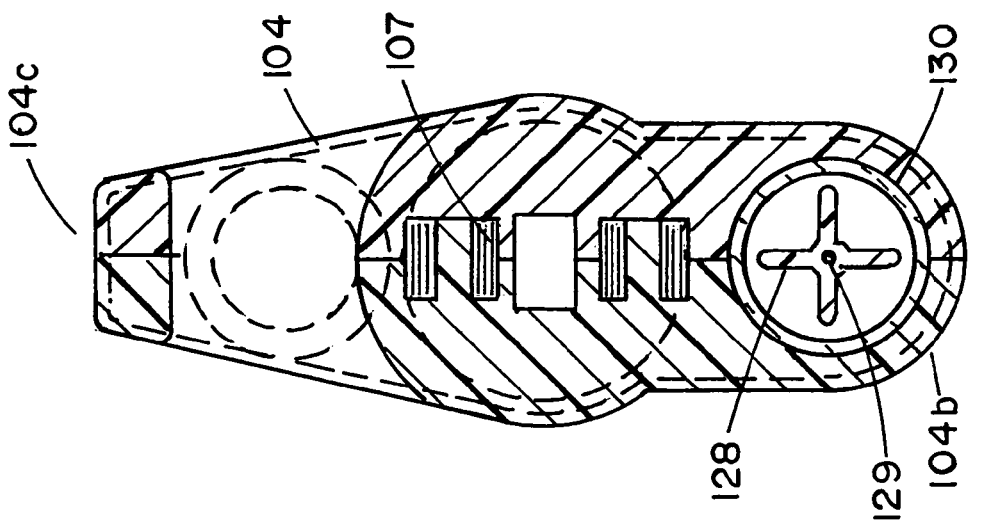
FIG. 8 is a cross-sectional view taken along lines 8-8 of FIG. 7.

As shown in FIG. 14, selector knob 180 is provided with a plurality of circumferentially spaced apart indexing cavities 200 that closely receive the end of an indexing finger 202a of an outwardly extending locking arm 202, which forms a part of the flow control means of the invention and functions to prevent rotation selector knob 180. (FIGS. 6, 13 and 10) Finger 202a is continuously urged into a selected one of the indexing cavities 200 formed in knob 180 by a coiled spring 204 (FIGS. 6 and 13). In order to permit rotation of knob 180, arm 202 must be pushed inwardly against the urging of spring 204.

In a similar manner, rotation of the macro rate selector knob 190 will permit each of the spaced outlets of the macro channels to selectively be aligned with a selected one of the outlets 170a, 170b, 170c, 170d and 170e of the rate control cover 162. The fluid can then flow into a selected one of the plurality of passages 194a, 194b, 194c, 194d and 194e formed in the micro rate selector knob 190, into axially extending passageway 196, into the administration line via a circumferentially extending fluid flow passageway 205, via a passageway 205a formed in housing portion 104b (see FIGS. 7 and 17) and then on to the patient at a precise macro rate of flow. To assist in rotating knob 190, the knob is provided with a finger gripping bar 191 (FIG. 1).

As shown in FIG. 17, selector knob 190 is provided with a plurality of circumferentially spaced apart indexing cavities 206 that closely receive the end of an indexing finger 208a of an outwardly extending locking arm 208, which forms a part of the flow control means of the invention and functions to prevent rotation selector knob 190 (FIGS. 6 and 13). Finger 208a is continuously urged into a selected one of the indexing cavities 206 formed in knob 190 by a coiled spring 210 (FIGS. 6 and 13). In order to permit rotation of knob 190, arm 208 must be pushed inwardly against the urging of spring 210.

Figure 4:
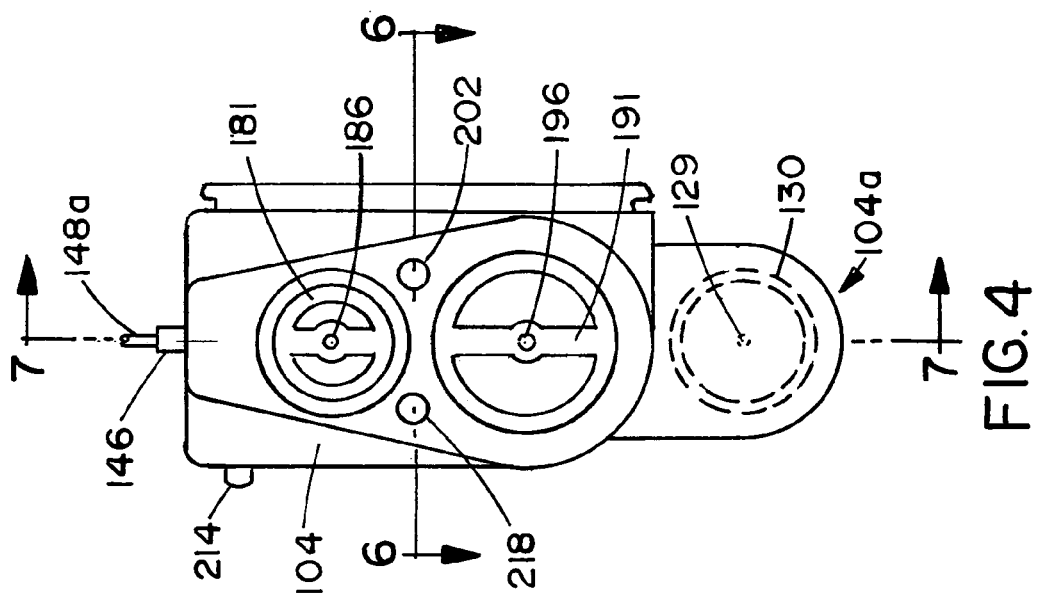
FIG. 4 is a front view of the fluid-dispensing device shown in FIGS. 1 and 2.
Figure 3:
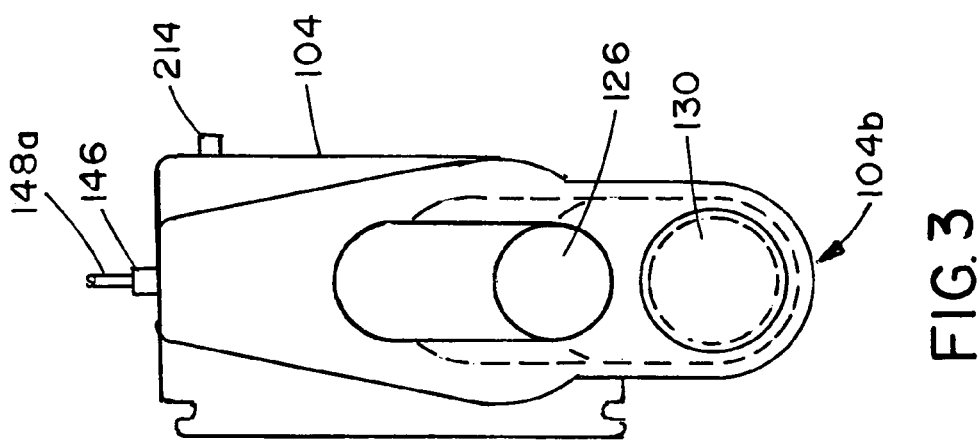
FIG. 3 is a rear view of the fluid-dispensing device shown in FIGS. 1 and 2.
Figure 11:
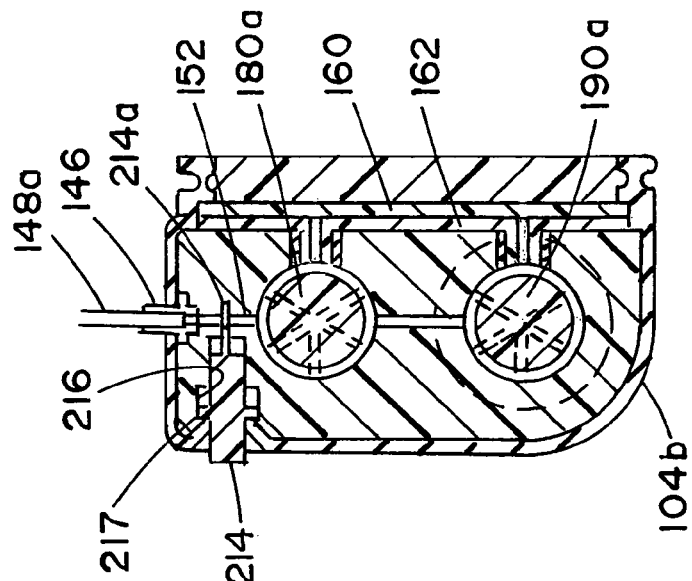
FIG. 11 is a cross-sectional view taken along lines 11-11 of FIG. 7.
Figure 10:
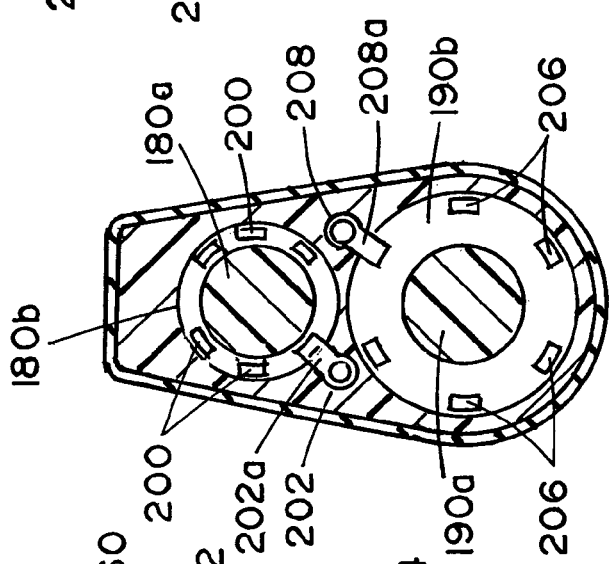
FIG. 10 is a cross-sectional view taken along lines 10-10 of FIG. 7.
Figure 9:
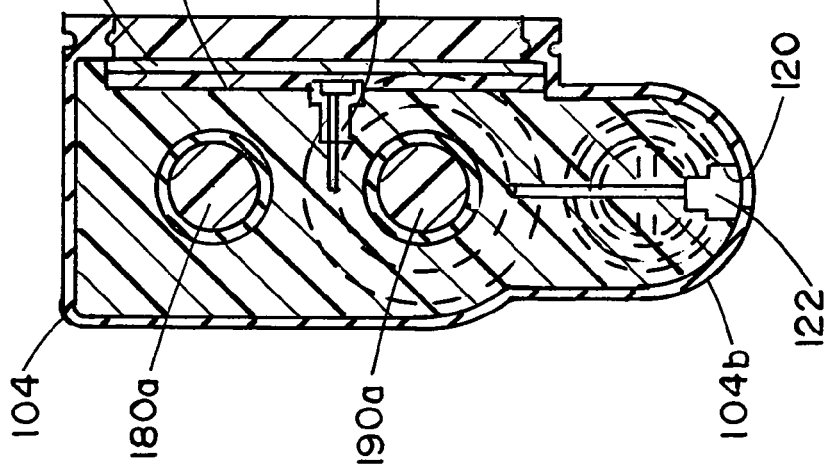
FIG. 9 is a cross-sectional view taken along lines 9-9 of FIG. 7.

The apparatus of this latest form of the invention also includes disabling means for irrevocably disabling the device and rendering it inert. Referring to FIGS. 1, 4 and 11, this disabling means here comprises a disabling shaft 214 that is telescopically movable within a passageway 216 formed within housing portion 104b. As best seen in FIG. 11, shaft 214 has a distal end 214a, which, upon insertion of the shaft distal end into passageway 152, will block fluid flow through the passageway. A friction fit retainer 216 normally holds shaft 214 in the retracted position.

The details of the construction of the important rate control plate, or member 160 of the invention and the various methods of making the rate control plate will now be considered. With respect to materials, the most appropriate materials for constructing the rate control plate are medical grade polymers. These types of polymers include thermoplastics, duroplastics, elastomers, polyurethanes, acrylics and epoxies. In other variations, the materials used for the flow control plate may be made of glass or silica. In further variations, the flow control component may be made of metals or inorganic oxides.

Using the foregoing materials, there are several ways that the flow control channels can be made. These include injection molding, injection-compression molding, hot embossing and casting. The techniques used to make these imbedded fluid channels are now commonplace in the field of microfluidics, which gave rise to the lab-on-a-chip, bio-MEMS and micro-total analysis systems (μ-TAS) industries. Additionally, depending on the size of the fluid channels required for a given flow rate, more conventional injection molding techniques can be used.

The first step in making the channels using an injection molding or embossing process is a lithographic step, which allows a precise pattern of channels to be printed on a "master" with lateral structure sizes down to 0.5 ☐m. Subsequently, electroforming is preformed to produce the negative metal form, or mold insert. Alternatively for larger channel systems, precision milling can be used to make the mold insert directly. Typical materials for the mold insert or embossing tool are nickel, nickel alloys, steel and brass. Once the mold insert of embossing tool is fabricated, the polymer of choice may be injection molded or embossed to yield the desired part with imprinted channels.

Alternatively, channels can be made by one of a variety of casting processes. In general, a liquid plastic resin, for example, a photopolymer can be applied to the surface of a metal master made by the techniques described in the preceding paragraph and then cured via thermal or ultraviolet (UV) means. After hardening, the material is then "released" from the mold to yield the desired part. Additionally, there are similar techniques available that utilize CAD data of the desired channel configuration and direct laser curing of a liquid monomer to yield a polymerized and solidified part with imbedded channels. This process is available by contract, from, by way of example, example MicroTEC, mbH of Duisburg Germany.

In order to seal the flow control channels, a planar top plate may be used. In this instance, the channel system may be sealed with a cover, or top plate, such as cover 162, which is here defined as any type of suitable cover that functions to seal the channel. The top plate may be sealably interconnected with the base which contains the flow channels by several means, including thermal bonding, sonic welding, laser welding, adhesive bonding and vacuum application.

Thermal bonding may be preformed by using a channel base plate material and planar top cover that are made of similar polymeric materials. In this case the two substrates are placed in contact with one another, confined mechanically and heated to 2-5° C. above their glass transition temperature. Following a holding period sufficient enough for the polymer molecules of the two surfaces interpenetrate with one another, the temperature is slowly reduced and a stress free bonded interface with imbedded micro channels is yielded.

Additionally, the top plate, or cover may be bonded to the base plate through the use of one or more suitable bonding materials or adhesives. The bonding material or adhesive may be of the thermo-melting variety or of the liquid or light curable variety. For thermo-melting adhesives, the adhesive material is melted into the two apposed surfaces, thereby interpenetrating these surfaces and creating a sealed channel structure.

Further, liquid curable bonding materials or adhesives and light curable bonding materials or adhesives may be applied to one of the surfaces, for example the cover. Subsequently, the other surface is brought into contact with the coated surface and the adhesive is cured by air exposure or via irradiation with a light source. Liquid curable bonding materials or adhesives may be elastomeric, for example, thermoplastic elastomers, natural or synthetic rubbers, polyurethanes, and silicones. Elastomeric bonding materials may or may not require pressure to seal the channel system. They may also provide closure and sealing to small irregularities in the apposed surfaces of the channel system.

A channel system may also be formed and sealed in cases where two surfaces are being joined and one of the surfaces has one or more apertures. In order to promote bonding between these two surfaces, a vacuum may be applied to the apertures. Bonding may then be accomplished by thermal methods or after previously having applied a bonding material or adhesive.

While the rate control plate, or base member 160 can be constructed in various sizes, a rate control chip which is rectangular in shape and approximately 11 cm long and approximately 5 cm wide is suitable for the present application. Similarly, while the depth of the channels can vary depending upon the end use of the device, as a general rule the depth of the channels is on the order of approximately 10-100 um.

As previously mentioned, the cross section of the set of channels may vary in area over the members of the set of individual channels so as to achieve the specified flow rate of a particular channel. The cross section may also vary over the length of any particular channel so as to achieve the specified flow rate for the particular channel. Some examples of typical channel cross sections are square, rectangular, elliptical, circular, semi-circular and semi-elliptical. Channel cross sections may also be more complicated than those noted explicitly here.

A typical rate control system of the invention will, by way of example, be able to deliver fluid at six specified flow rates as, for example 0.25, 0.5, 1.0, 2.0 and 5.0 ml/hr. For optimum performance, the flow rate should be constant and within 10% of the desired specified value.

In operation, the flow of fluid through the flow control channels is controlled by taking advantage of the viscous drag imposed on the moving fluid by the walls of the channels. For a given imposed pressure and channel cross section, the longer the channel, the smaller the flow rate. The pressure required to achieve the desired flow rates in the micron channels is preferably in the range of from 0.01 to 1 ATM. However, for some applications it may be desirable to exceed these limits.

The path that the micro channels take in any given rate control plate, or chip may be straight, a single meander or two or more meanders. The turns of the meanders may be of any angle from approximately 45° to approximately 220°. The runs of straight path between turns of the meanders may be of any length that the chip can accommodate, but these straight runs would typically be from 50 um to 500 um in length.

Referring particularly to FIG. 7, reservoir 105a can also be filled using an alternate form of fill means of the invention that comprises septum fill means which includes the previously identified septum 122. Septum 122 can be pierced by the piercing needle of a conventional syringe (not shown). In a conventional manner the fluid contained within the syringe can be caused to flow through the piercing needle which has pierced septum 122, into passageway 118, thence into passageway 140. From passageway 140 the fluid will flow into inlet 105b of reservoir 105a.

Figure 27:
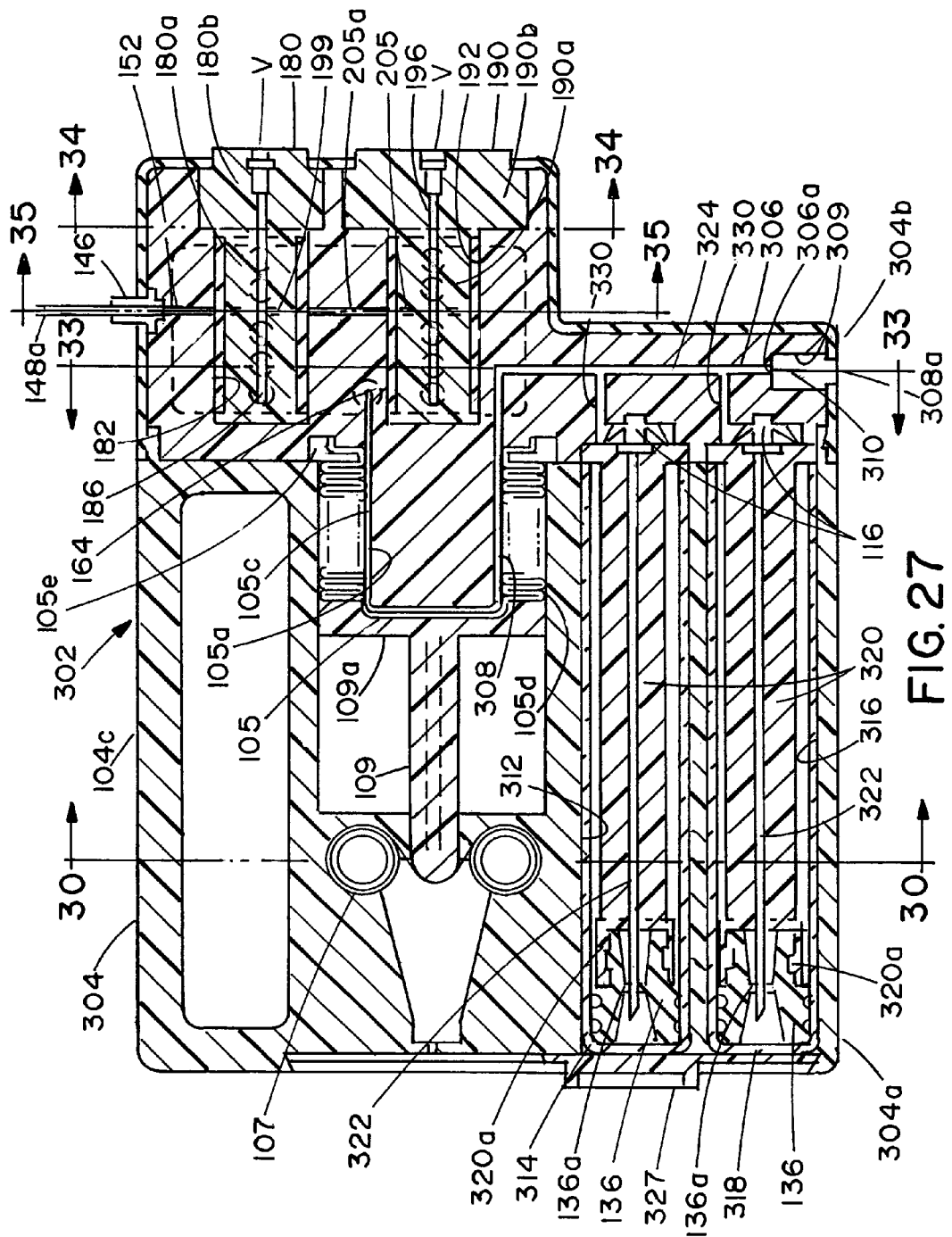
FIG. 27 is a longitudinal cross-sectional view of an alternate form of the fluid dispensing device of the present invention.
Figure 29:
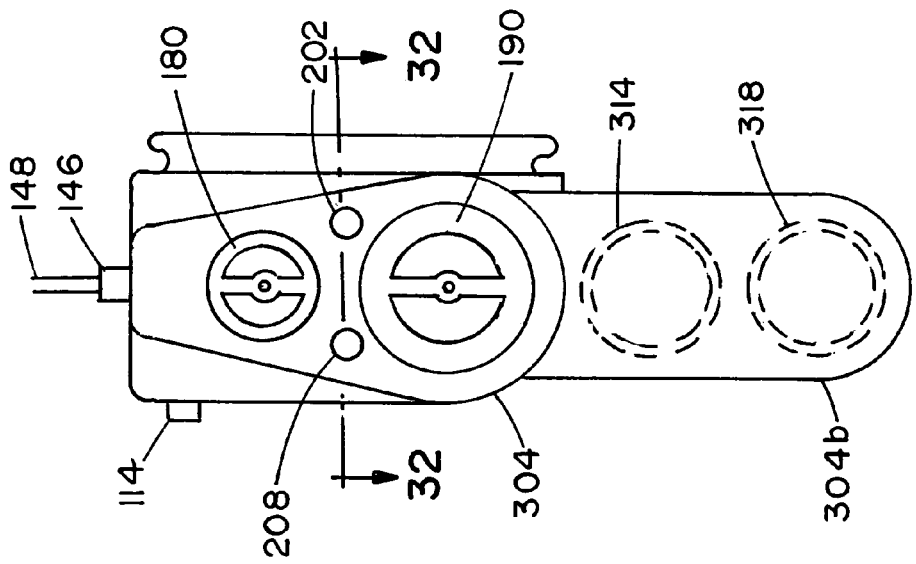
FIG. 29 is a front view of the fluid-dispensing device shown in FIG. 27.
Figure 28:
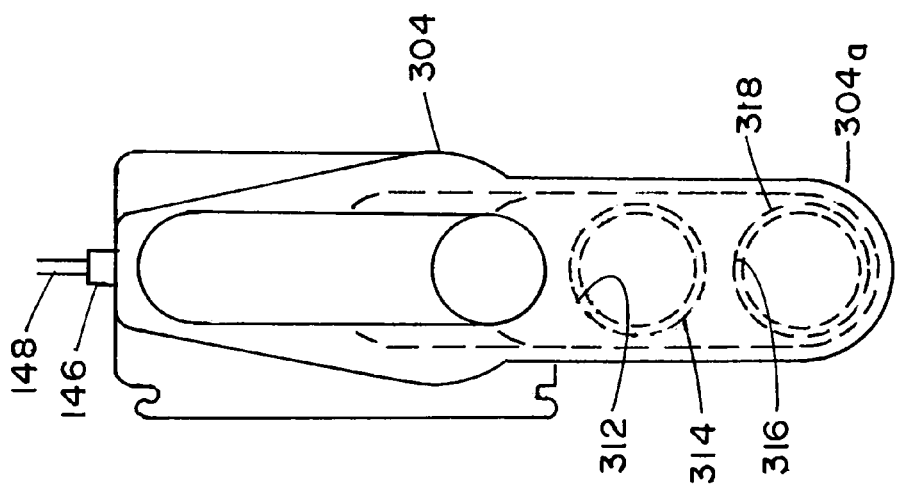
FIG. 28 is a rear view of the fluid-dispensing device shown in FIG. 27.
Figure 32:
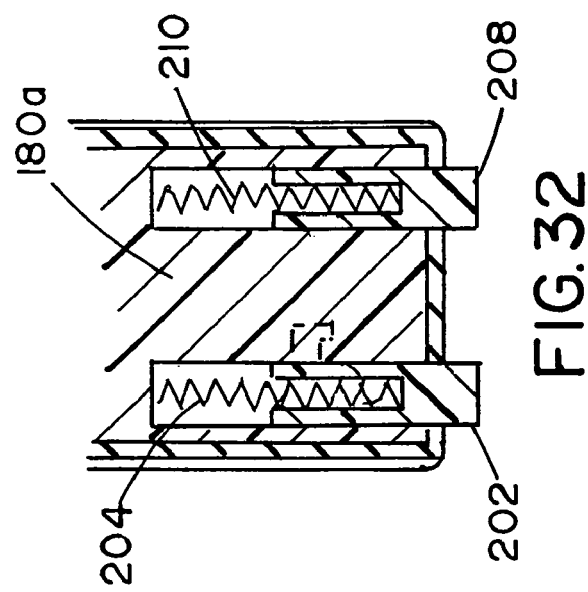
FIG. 32 is a cross-sectional view taken along lines 32-32 of FIG. 29.
Figure 31:
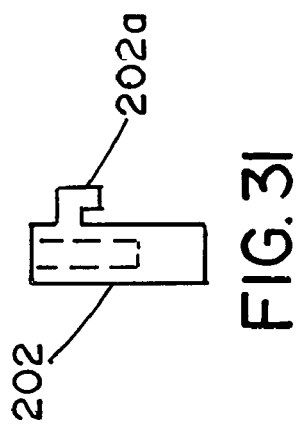
FIG. 31 is a side view of one of the locking arms of the device.
Figure 30:
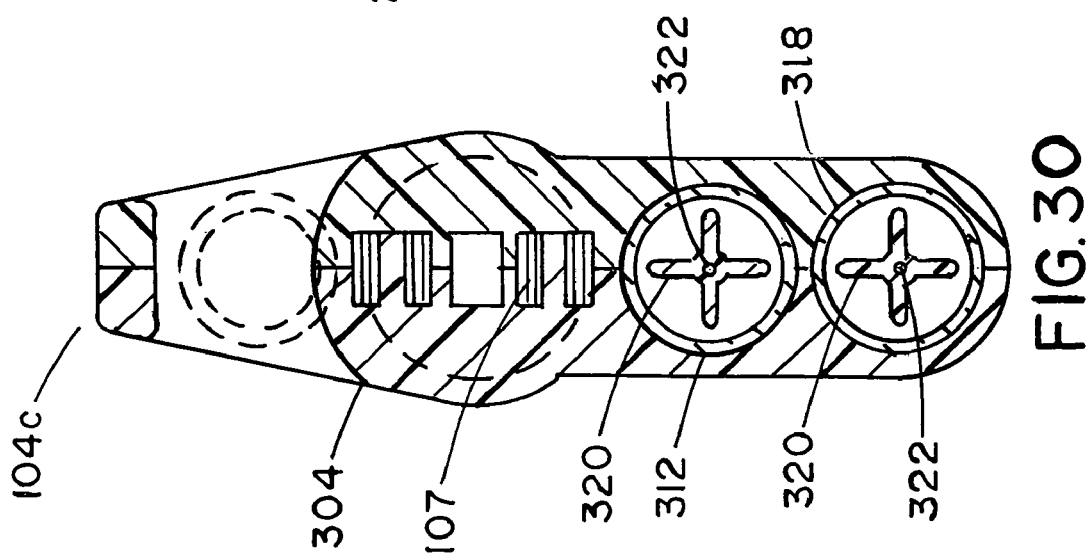
FIG. 30 is a cross-sectional view taken along lines 30-30 of FIG. 27.
Figure 36:
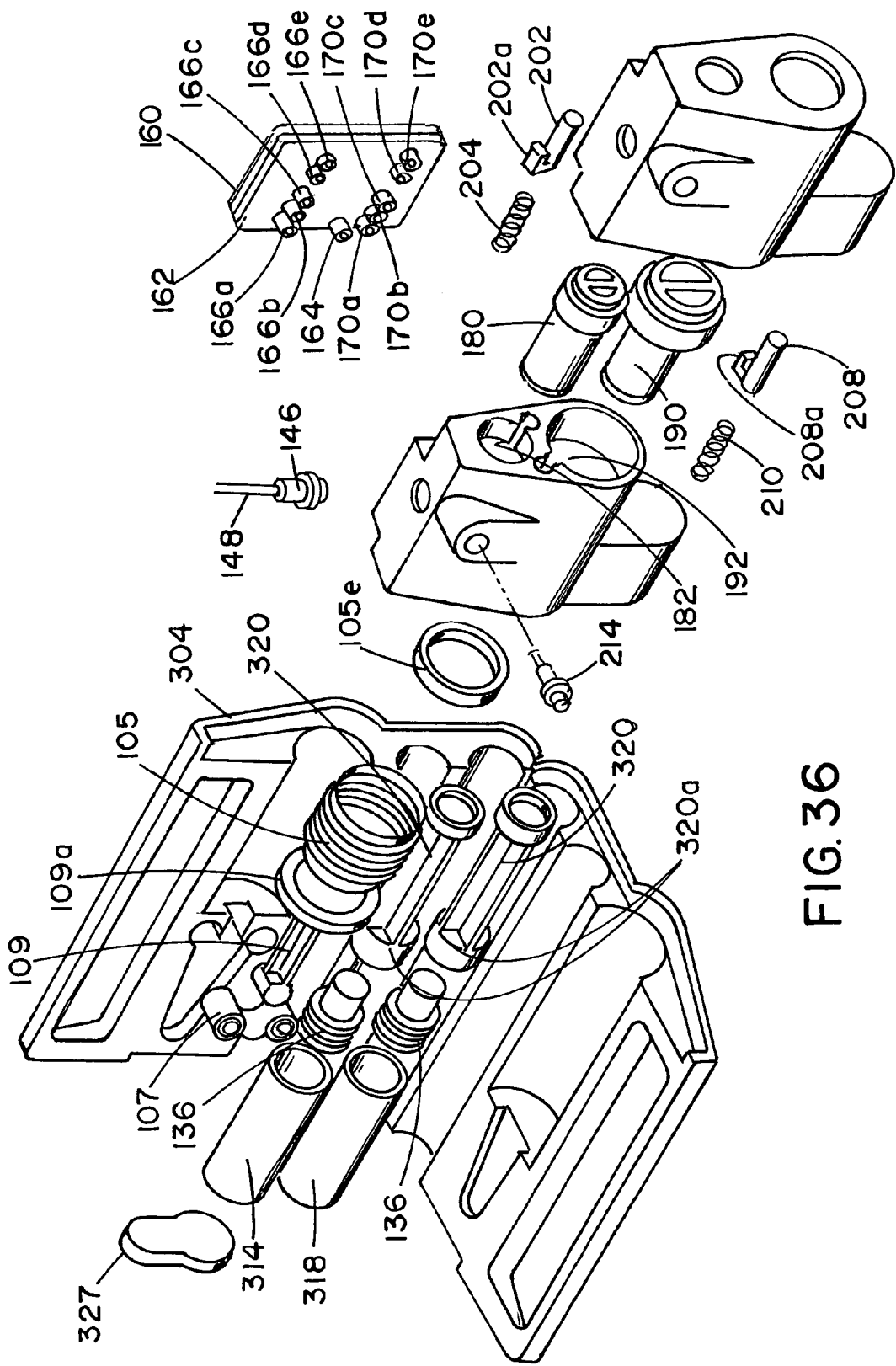
FIG. 36 is a generally perspective, exploded view of the fluid dispensing device shown in FIG. 27.

Turning next to FIGS. 27 through 46, another form of the apparatus of the present invention is there illustrated and generally designated by the numeral 302. This apparatus is similar in some respects to the apparatus shown in FIGS. 1 through 26 and like numerals are used in FIGS. 27 through 46 to identify like components. As best seen in FIG. 27, the primary difference between this latest form of the invention and that shown in FIGS. 1 through 26 concerns the provision of a differently configured reservoir fill means for filling the device reservoir. More particularly, as will presently be described in greater detail, this alternate form of fill means comprises two fill vials or containers, rather than one.

As best seen in FIG. 27, the apparatus here comprises an outer housing 304 having first and second portions 304a and 304b respectively. Disposed within outer housing 304a is an inner, expandable housing 105 which is identical in construction and operation to that described in connection with the embodiment of FIGS. 1 through 26.

Also disposed within second portion 304a of the outer housing is the novel stored energy means of the invention for acting upon inner expandable housing 105 in a manner to cause the fluid contained within fluid reservoir 105a thereof to controllably flow outwardly of the housing. In this latest form of the invention, this stored energy means is also identical in construction and operation to that previously described and comprises a constant force spring 107.

With regard to the fill means of this latest form of the invention, which is also carried by first portion 304a of the outer housing, this important fill means functions to fill the reservoir 105a with the fluid to be dispensed. This fill means here comprises the previously described septum fill means, which is identical to that previously described and also includes a vial fill means which includes two, rather than the one, fill vial or fill container.

As to the septum fill means, as illustrated in FIG. 27, second housing portion 304b includes a fluid passageway 306 which is in communication with inlet 308 of fluid reservoir 105a. Proximate its lower end 306a, fluid passageway 306 communicates with a cavity 309 formed within the second housing portion. Disposed within cavity 309 is a pierceable septum 310 that comprises a part of the septum fill means of this latest form of the invention. As before, septum 310 is pierceable by the needle of the syringe which contains the medicinal fluid to be dispensed and which can be used in a conventional manner to fill or partially fill reservoir 105a via passageway 306.

First portion 304a of the housing also includes a first chamber 312 for telescopically receiving a first medicament containing fill vial 314 and a second chamber 316 for receiving a second medicament containing vial 318. The fill vials 314 and 318 are of identical construction to vial 130 of the earlier described embodiment. Telescopically receivable within each of the fluid chambers of the vials are elongated supports 320. Each of the elongated supports 320 has an integrally threaded end portion 320a and each carries a longitudinally extending, elongated hollow needle 322. Each of the hollow needles 322 has a flow passageway that communicates with a fluid passageway 324 provided in housing portion 304b (FIG. 27). First chamber 312, second chamber 316, elongated supports 320, and hollow needles 322 together comprise the alternate form of the vial fill means of the apparatus of the invention. The method of operation of this alternate form of fill means will presently be described.

A number of beneficial agents can be contained within vials 314 and 318 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

Forming another very important aspect of the apparatus of this latest form of the invention is a novel flow control means that are carried by second portion 304b of outer housing 304. This flow control means which is identical in construction and operation to that described in connection with the first embodiment of the invention, functions to precisely control the outwardly rate of fluid flow from reservoir 105a and toward the patient. As before, the flow control means comprises an assembly which includes a base plate, or rate control member 160 and a mating cover member 162 (FIG. 21). As illustrated in FIG. 22, flow rate control member, or base plate 160 is uniquely provided with a plurality of micro rate flow control channels 160a, 160b, 160c, 160d and 160e respectively, which are in communication with the spaced apart micro rate outlet ports of the cover member 162. Flow rate control member, or base plate 160 is also uniquely provided with a plurality of macro rate flow control channels 173a, 173b, 173c, 173d and 173e respectively, which are in communication with the spaced apart macro rate outlet ports of the cover member 162.

Also forming a part of the flow control means of this latest form of the invention is a micro rate selector knob 180 that is carried within a horizontal bore 182 formed in housing portion 304b. Selector knob 180 is of identical construction and operation to the selector knob described in connection with the first embodiment of the invention and is uniquely provided with a plurality of radially extending flow control channels 184a, 184b, 184c, 184d and 184e, each having an inlet port and an outlet port which is in fluid communication with an axially extending passageway 186. Axially extending passageway 186 is, in turn, in fluid communication with administration line 148, which is also of identical construction and operation to that described in connection with the first embodiment of the invention.

Micro selector knob 180, which comprises a part of the selector means of this latest form of the invention, functions to selectively align one of the inlets of the radially extending flow control channels of the selector knob with a selected one of the spaced apart micro rate fluid outlets 166a, 166b, 166c, 166d and 166e of the rate control cover 162 (FIG. 18).

Also forming a part of the flow control means of this latest form of the invention is a macro rate selector knob 190 that is carried within a horizontal bore 192 formed in housing portion 304b. Selector knob 190 is also of identical construction and operation to selector knob 190 as described in connection with the first embodiment of the invention and is uniquely provided with a plurality of radially extending flow control channels 194a, 194b, 194c, 194d and 194e, each having an inlet port and an outlet port which it is in fluid communication with an axially extending passageway 196. Axially extending passageway 196 is, in turn, in fluid communication with administration line 148.

Selector knob 190, which also comprises a part of the selector means of this latest form of the invention, functions to selectively align one of the inlets of the radially extending flow control channels of the macro selector knob with a selected one of the spaced apart macro rate fluid outlets 170a, 170b, 170c, 170d and 170e of the rate control cover 162 (see FIG. 18).

In using the apparatus of this latest form of the invention, following removal of the vial cover 327, which forms a part of the first portion of housing 304 (FIGS. 27 and 36), vials 314 and 318 can be inserted into chambers 312 and 316 respectively. As the fill vials are so introduced and the plungers 136 are threadably interconnected with ends 320a of supports 320, the sharp ends of the elongated needles 322 will pierce the central walls 136a of the elastomeric plungers. Continuous movement of the vials into chambers 312 and 316 will cause the structural supports 320 to move the elastomeric plungers inwardly of the vial chambers. As the plungers move inwardly of the vials, the fluid contained within the vial chambers will be expelled therefrom into the hollow elongated needles 322. As best seen in FIG. 27, the fluid will then flow past umbrella type check valves 116 and into stub passageways 330 formed in second portion 304b of the apparatus housing. From passageways 330 the fluid will flow into passageway 324 and then into reservoir 105a of the bellows component 105 via inlet 308. It is to be understood that the vials 316 and 318 can contain the same or different medicinal fluids and can be introduced into their respective chambers either one at a time, or simultaneously.

It is also to be understood that, if desired, the reservoir of the bellows component can also be filled by alternate filling means of the character previously described which comprises a syringe having a needle adapted to pierce the pierceable septum 310 which is mounted within second portion 304b of the apparatus housing. As the reservoir 105a fills with fluid either from the fill vials or from the filling syringe, any gases trapped within the reservoir will be vented to atmosphere via vent means "V", mounted in portion 304b of the housing.

As the fluid flows into reservoir 105a, the bellows 105d will expand in a manner to exert a rearward pressure on the plunger end portion 109a of pusher member 109 causing it to move rearwardly. As the pusher member moves rearwardly, it will exert forces on spring member 107 causing it to it to expand from its retracted configuration shown in FIG. 27 to its expanded configuration. This rearward movement of pusher member 109 can be viewed through the volume indicator window 142 indicating that the reservoir has changed from an empty configuration to a filled configuration (FIG. 1).

As before selector knobs 180 and 190 are provided with a plurality of circumferentially spaced apart indexing cavities that closely receive the ends of the indexing fingers of outwardly extending locking arms 208, which forms a part of the flow control means of the invention and function to prevent rotation of the selector knobs (see FIGS. 6 and 13). Similarly disabling means of the character previously described can be used to disable the apparatus of this latest form of the invention.

Turning next to FIGS. 37 through 46, still another form of the apparatus of the present invention is there illustrated and generally designated by the numeral 402. This alternate form of the apparatus of the invention is also similar in many respects to that shown in FIGS. 1 through 26 and like numerals are used in FIGS. 37 through 46 to identify like components. The primary difference between this latest form of the invention and that shown in FIGS. 1 through 26 is that the vial fill means for filling the device reservoir is of a different configuration from that used in both the first and second, previously described embodiments of the invention. More particularly, as will presently be described in greater detail, this alternate form of vial fill means comprises a vial cartridge having a hollow glass or plastic body portion that defines a fluid chamber that is closed by a pierceable, elastomeric septum.

Figure 37:
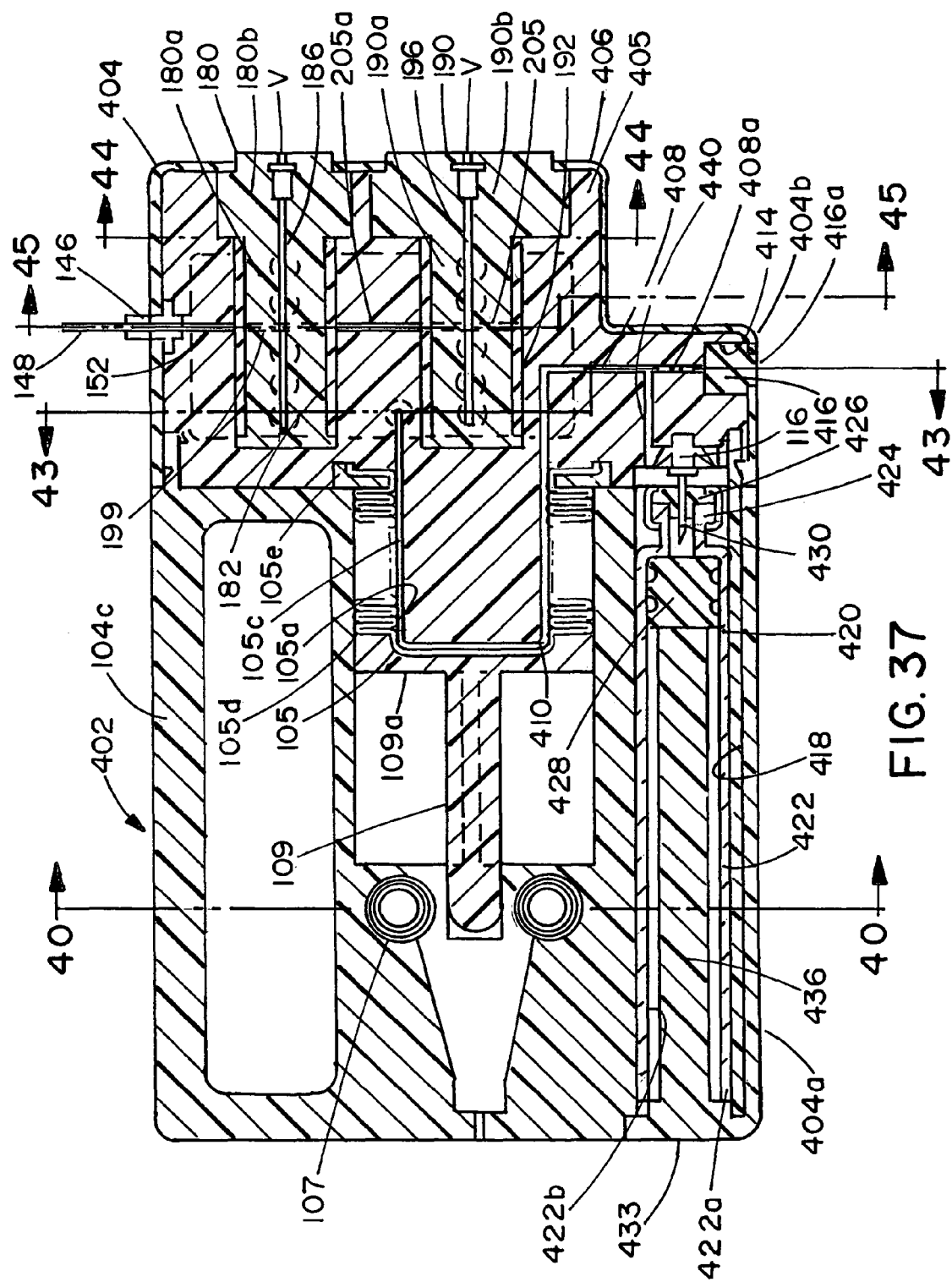
FIG. 37 is a longitudinal cross-sectional view of still another form of the fluid dispensing device of the present invention.
Figure 39:
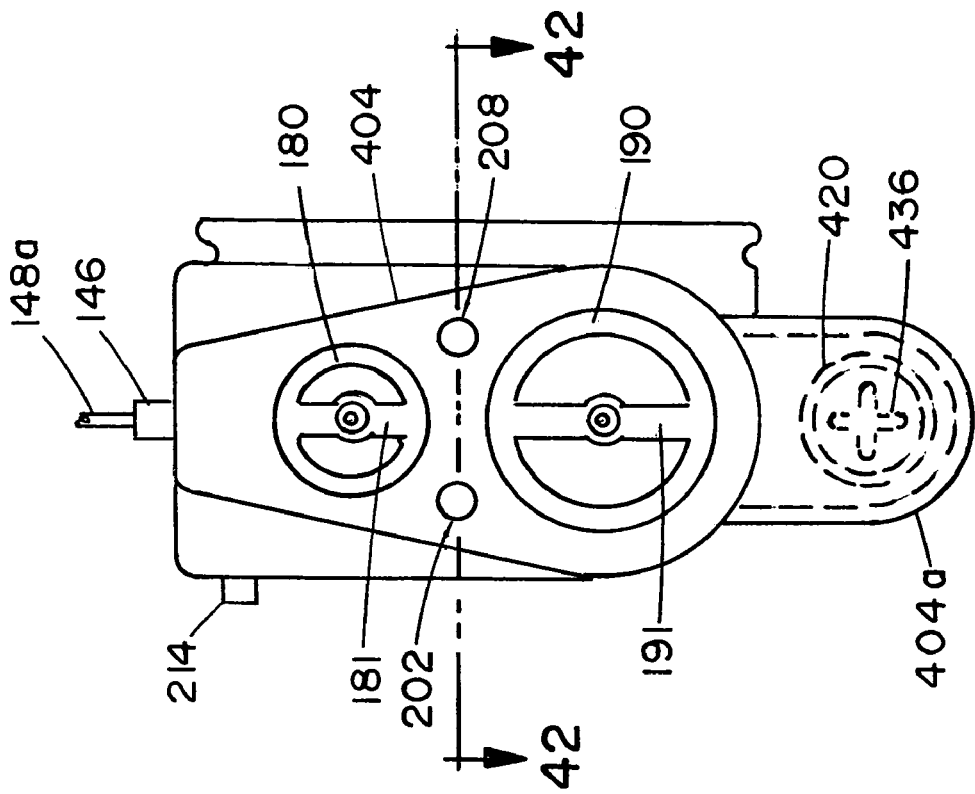
FIG. 39 is a front view of the fluid-dispensing device shown in FIG. 37.
Figure 38:
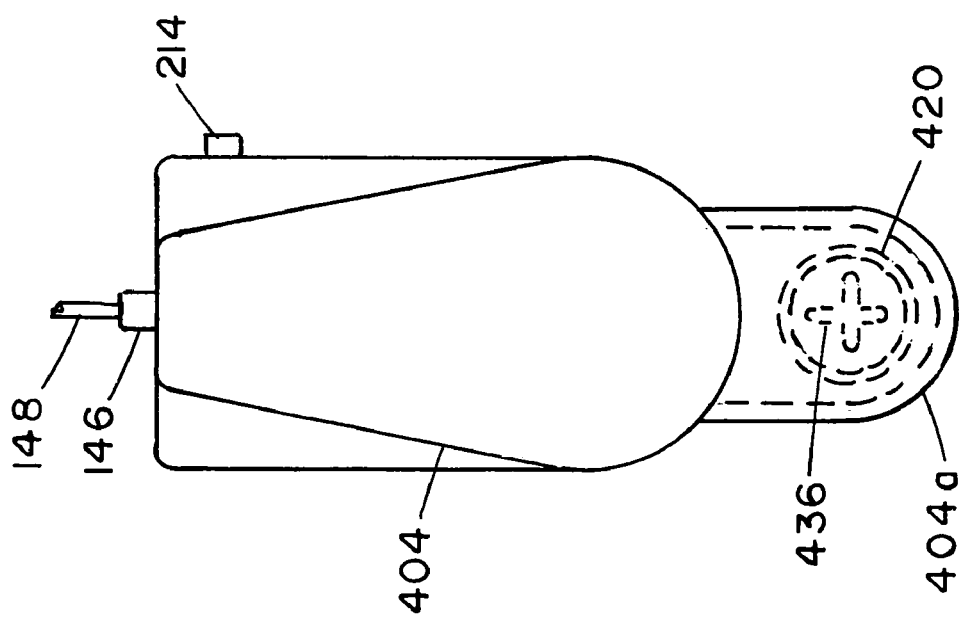
FIG. 38 is a rear view of the fluid-dispensing device shown in FIG. 37.
Figure 45:
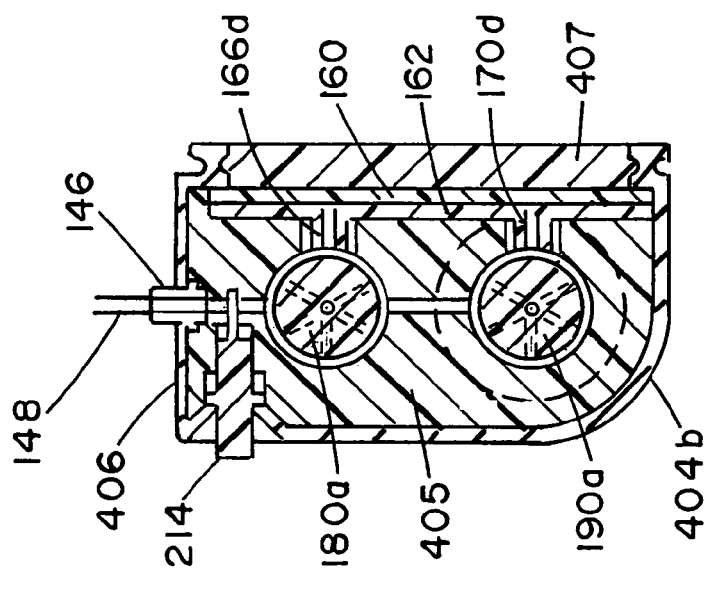
FIG. 45 is a cross-sectional view taken along lines 45-45 of FIG. 37.
Figure 44:
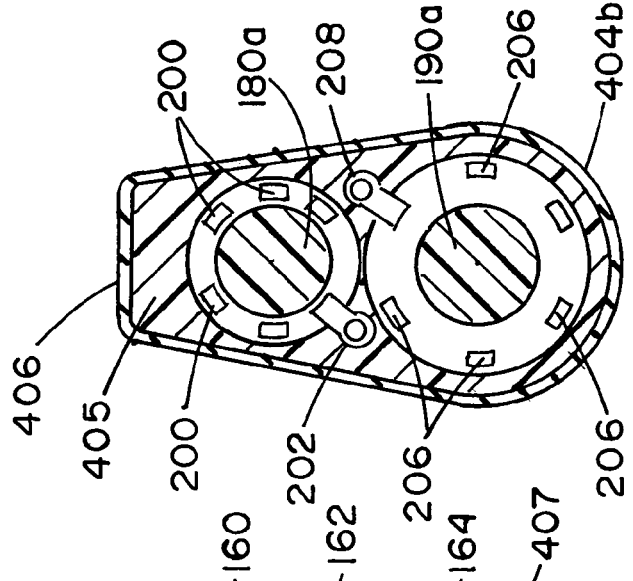
FIG. 44 is a cross-sectional view taken along lines 44-44 of FIG. 37.
Figure 43:
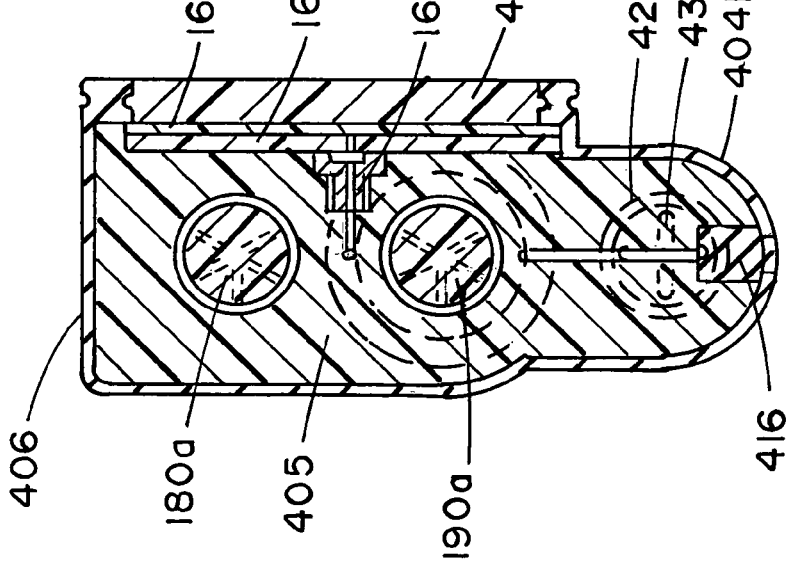
FIG. 43 is a cross-sectional view taken along lines 43-43 of FIG. 37.
Figure 46:
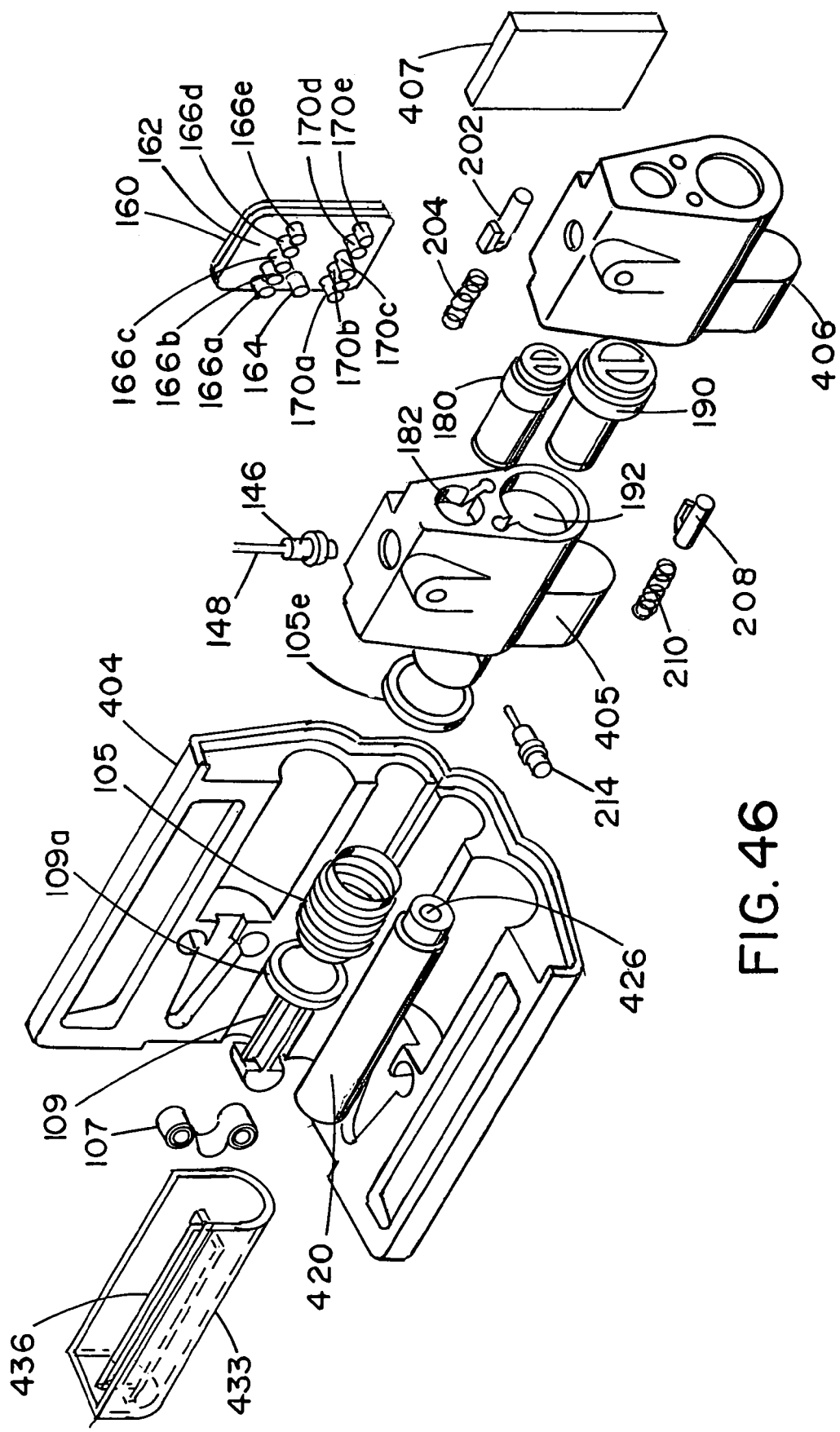
FIG. 46 is a generally perspective, exploded view of the fluid dispensing device shown in FIG. 37.

As best seen in FIG. 37, the apparatus here comprises an outer housing 404 having first and second portions 404a and 404b respectively. Disposed within outer housing 404 is an inner, expandable housing 105 which is identical in construction and operation to that described in connection with the embodiment of FIGS. 1 through 26.

Also disposed within housing 404 is the novel stored energy means of the invention for acting upon expandable housing 105 in a manner to cause the fluid contained within fluid reservoir 105a thereof to controllably flow outwardly of the housing. In this latest form of the invention, this stored energy means is also identical in construction and operation to that previously described and comprises a constant force spring 107.

With regard to the fill means of this latest form of the invention, which is carried by the first portion 404a of the outer housing, as before, this important fill means functions to fill the reservoir 105a with the fluid to be dispensed. This fill means here comprises the previously described septum fill means which is identical to that previously described, and also includes the previously mentioned, cartridge type vial fill vial which is of the construction best seen in FIG. 37 of the drawings. As to the septum fill means, as illustrated in FIG. 37, second portion 404b includes a fluid passageway 408 which is in communication with inlet 410 of fluid reservoir 105a. Proximate its lower end 408a, fluid passageway 408 communicates with a cavity 414 formed within the second portion 404b of the housing. Disposed within cavity 414 is a pierceable septum 416 that comprises a part of the septum fill means of this latest form of the invention. As before, septum 416 is held in position by a retainer 416a and is pierceable by the needle of the syringe which contains the medicinal fluid to be dispensed and which can be used in a conventional manner to fill or partially fill reservoir 105a via passageway 408.

First portion 404a of the housing also includes a first chamber 418 for telescopically receiving the previously mentioned cartridge fill vial, which is generally designated in the drawings by the numeral 420. As shown in FIG. 37, cartridge fill vial 420 comprises a hollow glass or plastic body portion 422 that defines a fluid chamber 422b. Fill vial 420 has an open first end 422a and a second end 424 that is closed by a pierceable, elastomeric septum 426. An elastomeric plunger 428 is reciprocally movable within fluid chamber 424. As shown in FIG. 37, a hollow needle 430 is mounted within second portion 404b of the device housing and is located proximate the inboard end of chamber 424. Hollow needle 430 is adapted to pierce septum 426 when the fill vial is inserted into chamber 418 and pushed into the position shown in FIG. 37.

A number of beneficial agents can be contained within vial 420 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

Forming an important aspect of the apparatus of this latest form of the invention is a novel flow control means that is carried by second portion 404b of outer housing 404. This flow control means which is identical in construction and operation to that described in connection with the first embodiment of the invention, functions to precisely control the outwardly rate of fluid flow from reservoir 105a and toward the patient.

As before, the flow control means comprises an assembly which includes a base plate, or rate control member 160 and a mating cover member 162 (FIG. 21). As illustrated in FIG. 22, flow rate control member, or base plate 160 is uniquely provided with a plurality of micro rate flow control channels 160a, 160b, 160c, 160d and 160e respectively, which are in communication with the spaced apart micro rate outlet ports of the cover member 162. Flow rate control member, or base plate 160 is also uniquely provided with a plurality of macro rate flow control channels 173a, 173b, 173c, 173d and 173e respectively, which are in communication with the spaced apart macro rate outlet ports of the cover member 162.

Also forming a part of the flow control means of this latest form of the invention is a micro rate selector knob 180 that is carried within a horizontal bore 182 formed in housing portion 404b. Selector knob 180 is of identical construction and operation to the selector knob described in connection with the first embodiment of the invention and is uniquely provided with a plurality of radially extending flow control channels 184*a*, 184*b*, 184*c*, 184*d* and 184*e*, each having an inlet port and an outlet port which is in fluid communication with an axially extending passageway 186. Axially extending passageway 186 is, in turn, in fluid communication with administration line 148, which is also of identical construction and operation to that described in connection with the first embodiment of the invention.

Micro selector knob 180, which comprises a part of the selector means of this latest form of the invention, functions to selectively align one of the inlets of the radially extending flow control channels of the selector knob with a selected one of the spaced apart micro rate fluid outlets 166*a*, 166*b*, 166*c*, 166*d* and 166*e* of the rate control cover 162 (FIG. 18).

Also forming a part of the flow control means of this latest form of the invention is a macro rate selector knob 190 that is carried within a horizontal bore 192 formed in housing portion 404*b*. Selector knob 190 is also of identical construction and operation to selector knob 190 as described in connection with the first embodiment of the invention and is uniquely provided with a plurality of radially extending flow control channels 194*a*, 194*b*, 194*c*, 194*d* and 194*e*, each having an inlet port and an outlet port which it is in fluid communication with an axially extending passageway 196. Axially extending passageway 196 is, in turn, in fluid communication with administration line 148.

Selector knob 190, which also comprises a part of the selector means of this latest form of the invention, functions to selectively align one of the inlets of the radially extending flow control channels of the macro selector knob with a selected one of the spaced apart macro rate fluid outlets 170*a*, 170*b*, 170*c*, 170*d* and 170*e* of the rate control cover 162 (see FIG. 18).

In using the apparatus of this latest form of the invention, following removal of the vial cover 433, which forms a part of the first portion of housing 404 (FIGS. 37 and 46), vial 420 can be inserted into chamber 418. As previously mentioned, plunger 428 is disposed within vial 420 and is moved by a support 436 of a vial cover 433 (FIG. 46) as the vial cover is mated with the apparatus housing. As plunger 428 moves inwardly of vial reservoir 424, the fluid contained in the reservoir will be forced through hollow needle 430, passed the umbrella check valve 116 mounted within third housing portion 405, into a stub passageway 440, into passageway 408 and finally into reservoir 105*a* of the bellows component 105 via inlet 410.

It is also to be understood that, if desired, the reservoir of the bellows component can also be filled by alternate filling means of the character previously described which comprises a syringe having a needle adapted to pierce the pierceable septum 416 which is mounted within second portion 404*b* of the apparatus housing. As the reservoir 105*a* fills with fluid either from the fill vials or from the filling syringe, any gases trapped within the reservoir will be vented to atmosphere via vent means "V", mounted in portion 404*b* of the housing.

As the fluid flows into reservoir 105*a*, the bellows 105*d* will expand in a manner to exert a rearward pressure on the plunger end portion 109*a* of pusher member 109 causing it to move rearwardly. As the pusher member moves rearwardly, it will exert forces on spring member 107 causing it to expand from its retracted configuration shown in FIG. 37 to its expanded configuration. This rearward movement of pusher member 109 can be viewed through the volume indicator window 142 indicating that the reservoir has changed from an empty configuration to a filled configuration (FIG. 1).

As before selector knobs 180 and 190 are provided with a plurality of circumferentially spaced apart indexing cavities that closely receive the ends of the indexing fingers of outwardly extending locking arms 208, which forms a part of the flow control means of the invention and function to prevent rotation of the selector knobs (see FIGS. 6 and 13). Similarly disabling means of the character previously described can be used to disable the apparatus of this latest form of the invention.

Figure 47:
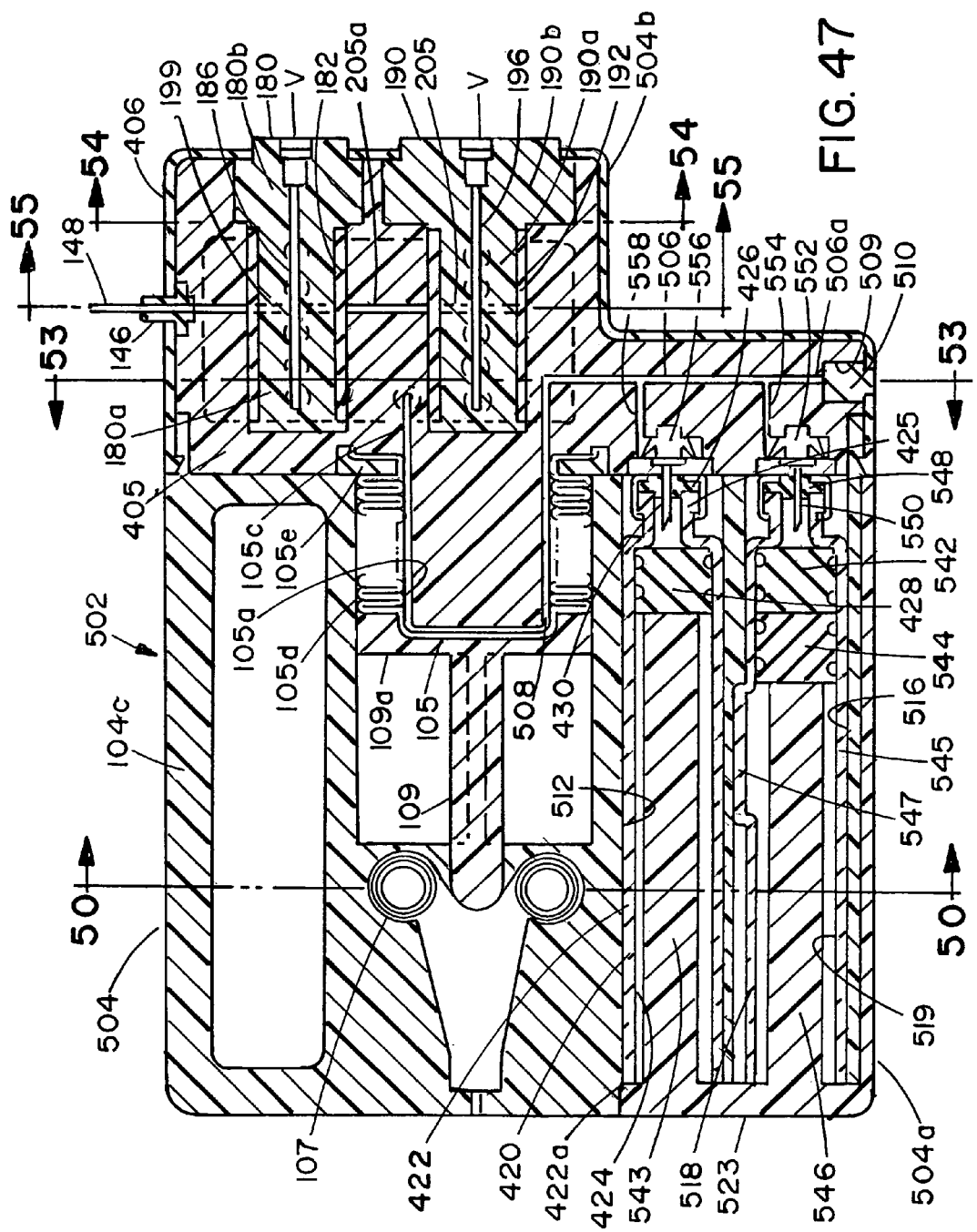
FIG. 47 is a longitudinal cross-sectional view of yet another form of the fluid dispensing device of the present invention.

Turning next to FIGS. 47 through 56, still another form of the apparatus of the present invention is there illustrated and generally designated by the numeral 502. This alternate form of the apparatus of the invention is similar in some respects to the apparatus shown in FIGS. 27 through 46 and like numerals are used in FIGS. 47 through 56 to identify like components. As best seen in FIG. 47, the primary difference between this latest form of the invention and that shown in FIGS. 27 through 46 concerns the provision of a differently configured reservoir fill means for filling the device reservoir. More particularly, as will presently be described in greater detail, this alternate form of fill means comprises two fill vials or containers, rather than one.

As best seen in FIG. 47, the apparatus here comprises an outer housing 504 having first and second portions 504*a* and 504*b* respectively. Disposed within outer housing 504*a* is an inner, expandable housing 105 which is identical in construction and operation to that described in connection with the embodiment of FIGS. 1 through 26.

Also disposed within second portion 504*a* of the outer housing is the novel stored energy means of the invention for acting upon inner expandable housing 105 in a manner to cause the fluid contained within fluid reservoir 105*a* thereof to controllably flow outwardly of the housing. In this latest form of the invention, this stored energy means is also identical in construction and operation to that previously described and comprises a constant force spring 107.

With regard to the fill means of this latest form of the invention, which is also carried by first portion 504*a* of the outer housing, this important fill means functions to fill the reservoir 105*a* with the fluid to be dispensed. This fill means comprises the previously described septum fill means which is identical to that previously described, and also includes a vial fill means which includes two, rather than the one, fill vial or fill container.

As to the septum fill means, as illustrated in FIG. 47, second housing portion 504*b* includes a fluid passageway 506 which is in communication with inlet 508 of fluid reservoir 105*a*. Proximate its lower end 506*a*, fluid passageway 506 communicates with a cavity 509 formed within the second housing portion. Disposed within cavity 509 is a pierceable septum 510 that comprises a part of the septum fill means of this latest form of the invention.

As before, septum 510 is pierceable by the needle of the syringe which contains the medicinal fluid to be dispensed and which can be used in a conventional manner to fill or partially fill reservoir 105*a* via passageway 506.

First portion 504*a* of the housing also includes a first chamber 512 for telescopically receiving the first medicament containing fill vial 420 and a second chamber 516 for receiving a second medicament containing vial 518. First vial 420, which is of identical construction to vial 420 of the earlier described embodiment, comprises a vial cartridge having a hollow glass or plastic body portion that defines a fluid chamber that is closed by a pierceable, elastomeric septum. However, the second vial cartridge 518 is of a uniquely different construction from the previously described medicament containing vials. More particularly, as will be discussed in greater detail hereinafter, this second vial cartridge is specially designed to enable the intermixing of a lypholized drug with suitable diluents prior to the delivery of the mixture to the fluid reservoir of the device.

A number of beneficial agents can be contained within vials 420 and 518 and can be controllably dispensed to the patient, including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

As in the earlier described embodiments of the invention, another very important aspect of the apparatus of this latest form of the invention is a novel flow control means that are carried by second portion 504b of outer housing 504. This flow control means which is identical in construction and operation to that described in connection with the first embodiment of the invention, functions to precisely control the outwardly rate of fluid flow from reservoir 105a and toward the patient. As before, the flow control means comprises an assembly which includes a base plate, or rate control member 160 and a mating cover member 162 (FIG. 21). As illustrated in FIG. 22, flow rate control member, or base plate 160 is uniquely provided with a plurality of micro rate flow control channels 160a, 160b, 160c, 160d and 160e respectively, which are in communication with the spaced apart micro rate outlet ports of the cover member 162. Flow rate control member, or base plate 160 is also uniquely provided with a plurality of macro rate flow control channels 173a, 173b, 173c, 173d and 173e respectively, which are in communication with the spaced apart macro rate outlet ports of the cover member 162.

Also forming a part of the flow control means of this latest form of the invention is a micro rate selector knob 180 that is carried within a horizontal bore 182 formed in member 406. Selector knob 180 is of identical construction and operation to the selector knob described in connection with the first embodiment of the invention and is uniquely provided with a plurality of radially extending flow control channels 184a, 184b, 184c, 184d and 184e, each having an inlet port and an outlet port which is in fluid communication with an axially extending passageway 186. Axially extending passageway 186 is, in turn, in fluid communication with administration line 148, which is also of identical construction and operation to that described in connection with the first embodiment of the invention.

Micro selector knob 180, which comprises a part of the selector means of this latest form of the invention, functions to selectively align one of the inlets of the radially extending flow control channels of the selector knob with a selected one of the spaced apart micro rate fluid outlets 166a, 166b, 166c, 166d and 166e of the rate control cover 162 (FIG. 18).

Also forming a part of the flow control means of this latest form of the invention is a macro rate selector knob 190 that is carried within a horizontal bore 192 formed in member 405. Selector knob 190 is also of identical construction and operation to selector knob 190 as described in connection with the first embodiment of the invention and is uniquely provided with a plurality of radially extending flow control channels 194a, 194b, 194c, 194d and 194e, each having an inlet port and an outlet port which it is in fluid communication with an axially extending passageway 196. Axially extending passageway 196 is, in turn, in fluid communication with administration line 148.

Selector knob 190, which also comprises a part of the selector means of this latest form of the invention, functions to selectively align one of the inlets of the radially extending flow control channels of the macro selector knob with a selected one of the spaced apart macro rate fluid outlets 170a, 170b, 170c, 170d and 170e of the rate control cover 162 (see FIG. 18).

With respect to cartridge fill vial 420, as before, this fill vial comprises a hollow glass or plastic body portion 422 that defines a fluid chamber 424. Fill vial 420 has an open first end 422a and a second end 424 that is closed by a pierceable, elastomeric septum 426. An elastomeric plunger 428 is reciprocally movable within fluid chamber 424. As shown in FIG. 47, a hollow needle to 430 is mounted within second portion 504b of the device housing and is located proximate the inboard end of chamber 424.

Figure 47A:
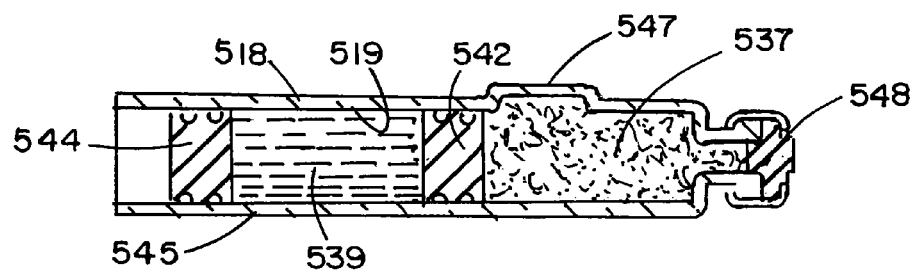
FIG. 47A is a longitudinal cross-sectional view of a specially designed vial cartridge that enables the intermixing of a lyophilized drug with a suitable diluent prior to the delivery of the mixture of the fluid reservoir of the device.
Figures 48, 49:
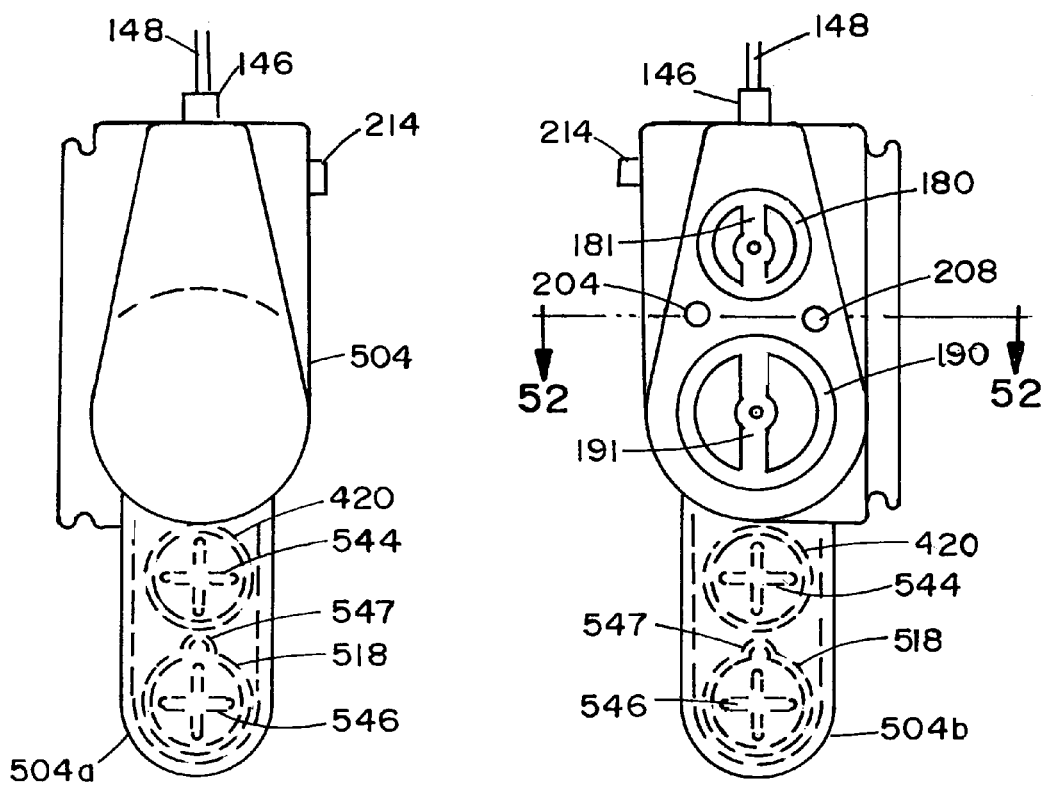
FIG. 48 is a rear view of the fluid-dispensing device shown in FIG. 47.
FIG. 49 is a front view of the fluid-dispensing device shown in FIG. 47.
Figure 55:
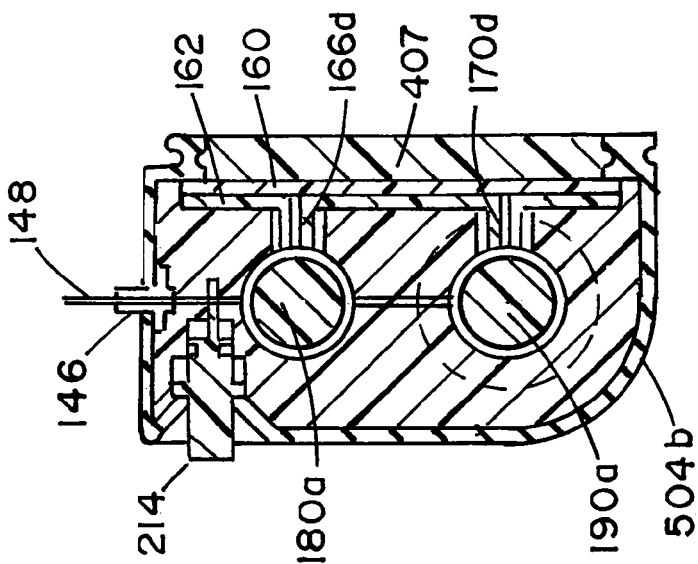
FIG. 55 is a cross-sectional view taken along lines 55-55 of FIG. 47.
Figure 54:
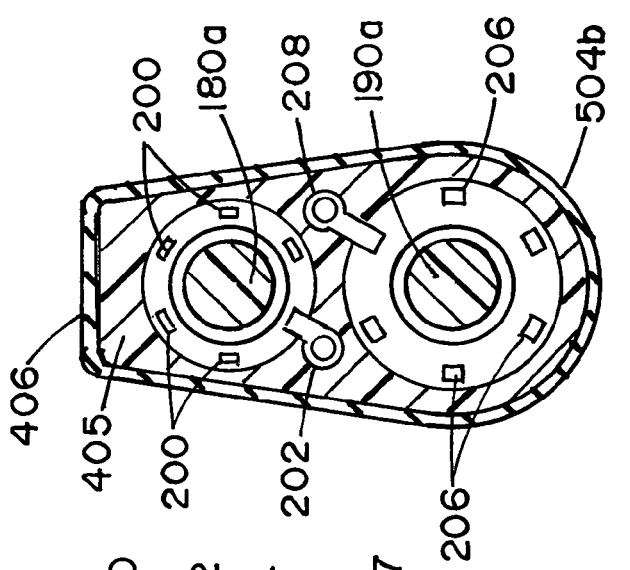
FIG. 54 is a cross-sectional view taken along lines 54-54 of FIG. 47.
Figure 53:
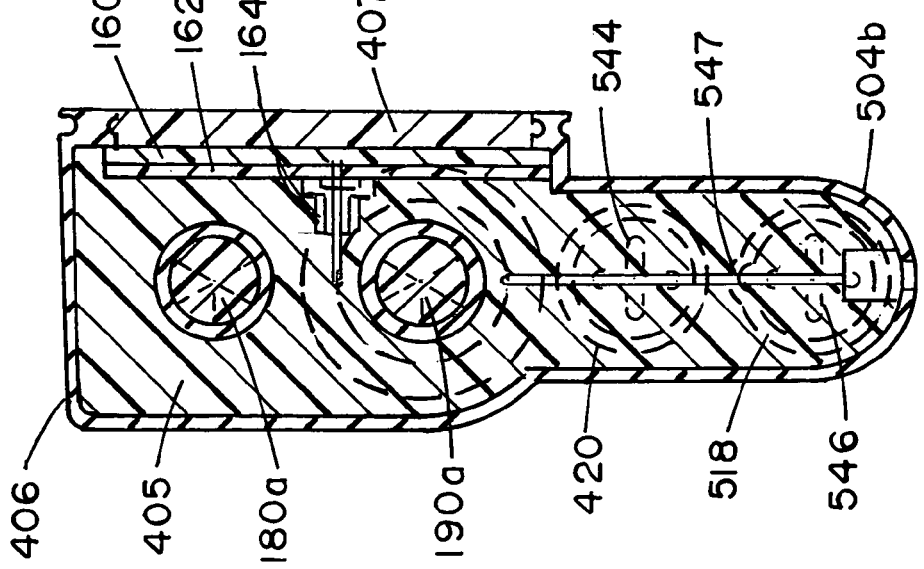
FIG. 53 is a cross-sectional view taken along lines 53-53 of FIG. 47.

With respect to second cartridge fill vial 518, this vial comprises a container of special design that includes a chamber 519 and uniquely contains a lyophilized drug 537 that is separated from a reconstituting fluid 539 by a barrier stopper 542 (FIG. 47A). Lyophilized drug 537 can, by way of example, comprise anti-infectives or various other types of beneficial agents. Second fill vial 518 also includes an elastomeric plunger 544 that is reciprocally movable within fluid chamber 519.

Figure 56:
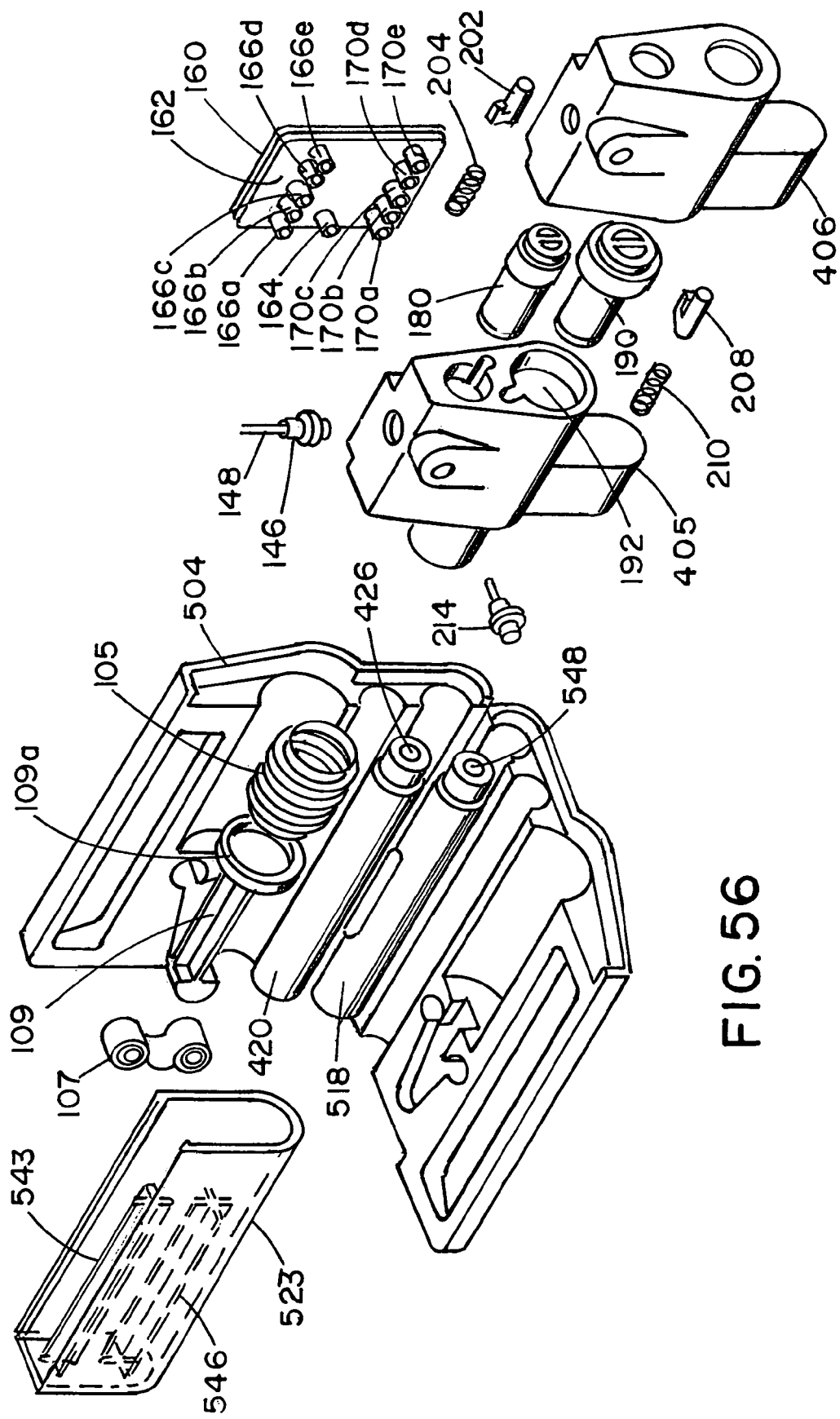
FIG. 56 is a generally perspective, exploded view of the fluid dispensing device shown in FIG. 47.

As illustrated in FIGS. 47 and 56, the removable cover 523 of the device housing includes a pair of spaced apart pusher members 544 and 546 which engage plungers 428 and 544 respectively to push them forwardly of their respective container chambers.

Considering in more detail the novel vial assembly 518, as best seen in FIG. 47A, this vial assembly comprises a vial 545 that is sealed at one end by plunger 544 and at the other end by a pierceable septum 548 (FIGS. 47 and 47A). Formed intermediate the ends of vial 545 is a raised outer wall portion 547 which permits fluid 539 to bypass a barrier stopper 542 as the barrier stopper is urged inwardly of the container by pressure exerted thereon by the fluid 539. Fluid 539 exerts pressure on barrier member 542 as a result of pusher member 546 exerting inward pressure on plunger 544, which pressure is, in turn, caused by the inward movement of plunger 544 as the cover 523 is mated with the apparatus housing.

A continued inward pressure exerted on plunger 544 will cause fluid 539 to flow past barrier member 542 via wall portion 547 so as to reconstitute lyophilized drug 537. Continued pressure exerted on plunger 543 will cause the reconstituted drug formed by the fluid 539 which has been intermixed with drug 537 to flow through a hollow needle 550 which is carried by housing portion 504b, past a lower check valve 552, into a stub passageway 554, then into passageway 506 and finally into the device reservoir 105a.

As the vial cover 523 is mated with the apparatus housing, pusher member 544 engages plunger 428 of vial 420 and moves it inwardly of vial reservoir 424. Continued inward movement of the pusher member causes the fluid contained in the reservoir to be forced through a hollow needle 430, passed the upper umbrella check valve 556 mounted within second housing portion 504b, into a stub passageway 558, into a passageway 506 and finally into the device reservoir.

As the fluid flows into reservoir 105a, it will compress the stored energy means, or constant force spring 107 in the manner previously described.

Upon opening the fluid delivery path to the administration set, the stored energy means, or member 107, will tend to return to its starting configuration thereby controllably urging fluid flow outwardly of reservoir 105a via the flow control means of the invention which functions in the manner previously described.

As in the earlier described embodiments, disabling means of the character previously described can be used to disable the apparatus of this latest form of the invention.

Figure 57:
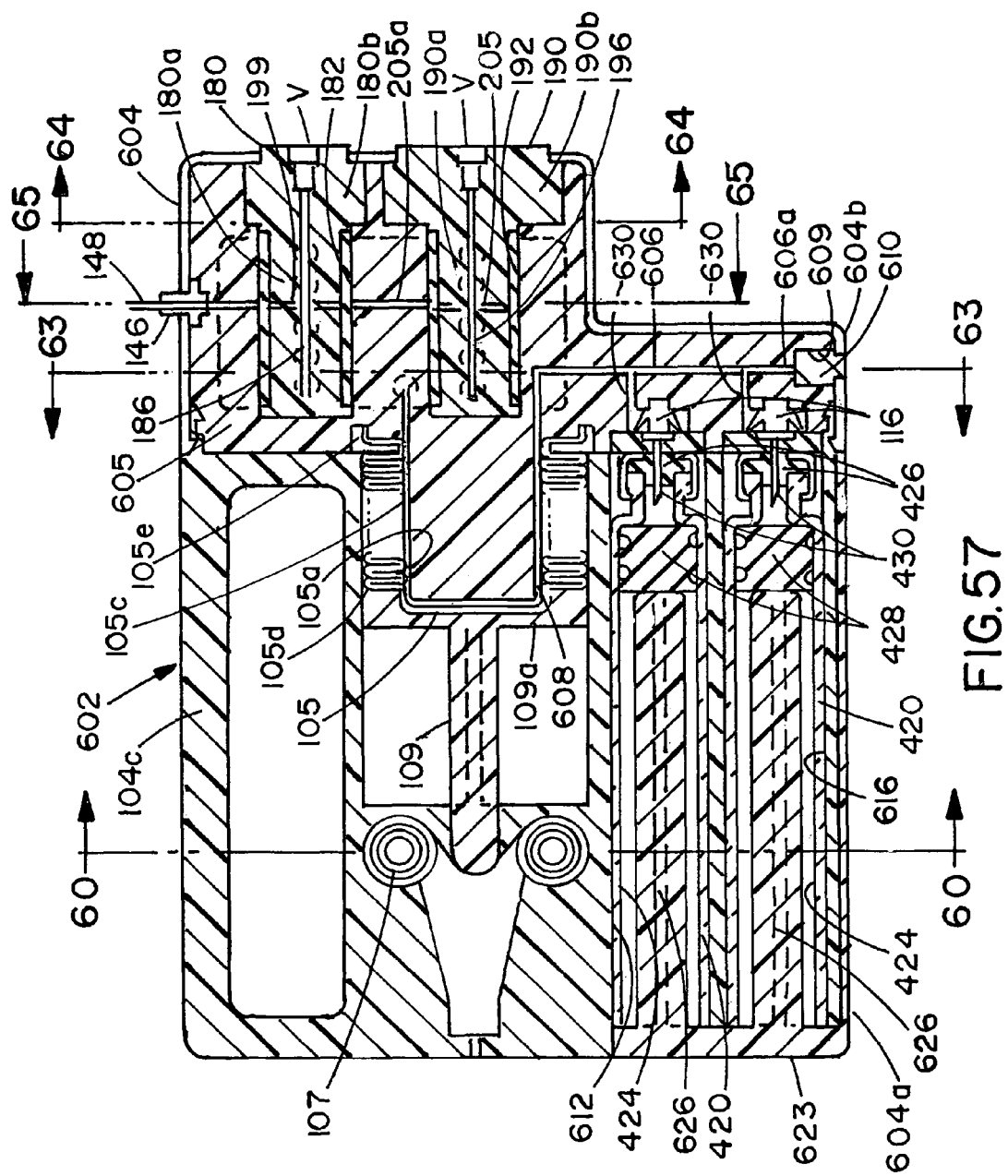
FIG. 57 is a longitudinal cross-sectional view of still another embodiment of the fluid dispensing device of the present invention.
Figure 59:
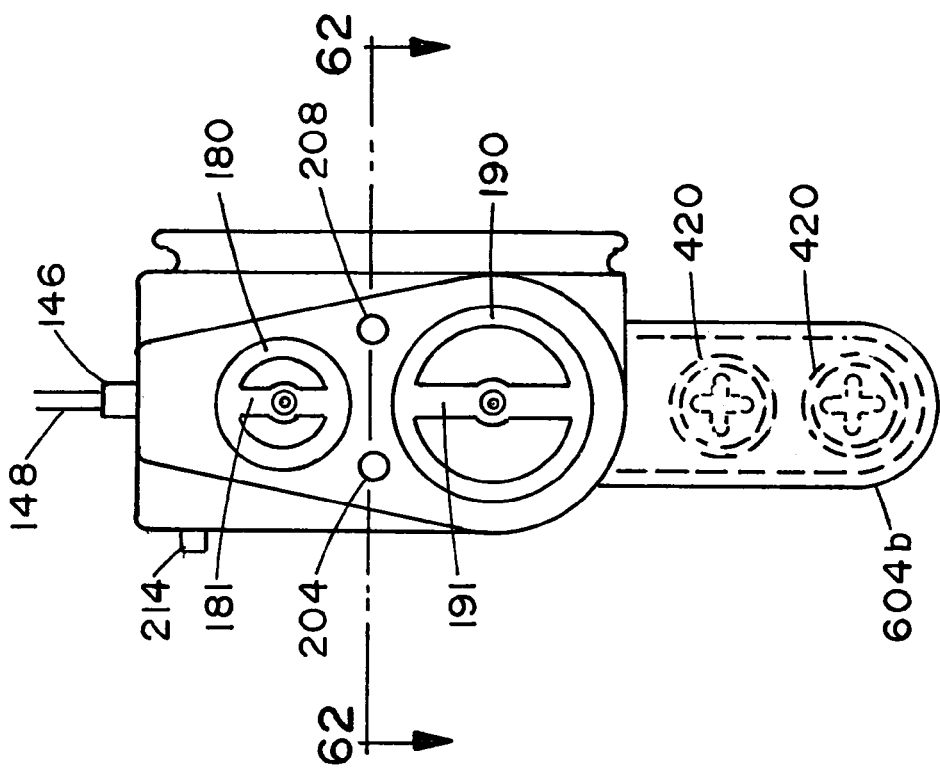
FIG. 59 is a front view of the fluid-dispensing device shown in FIG. 57.
Figure 58:
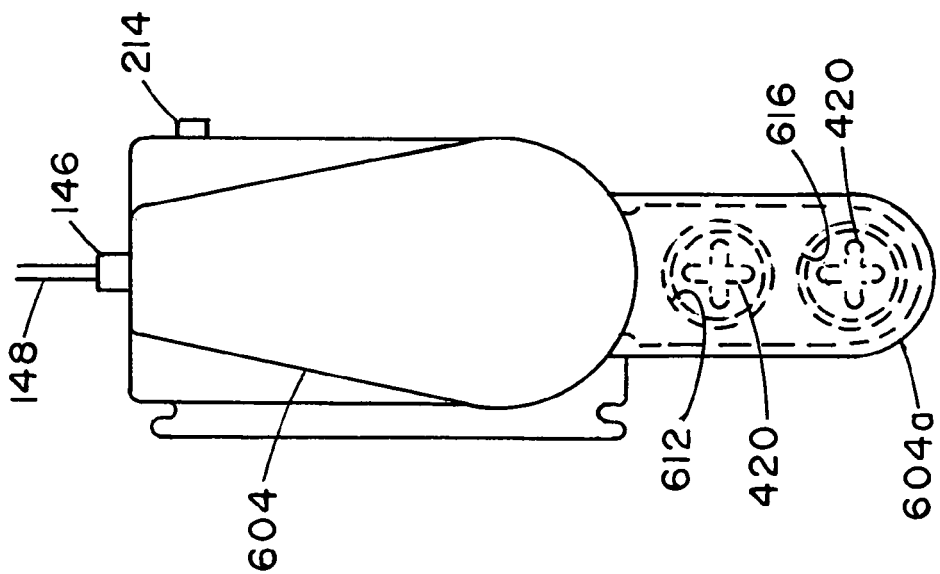
FIG. 58 is a rear view of the fluid-dispensing device shown in FIG. 57.
Figure 66:
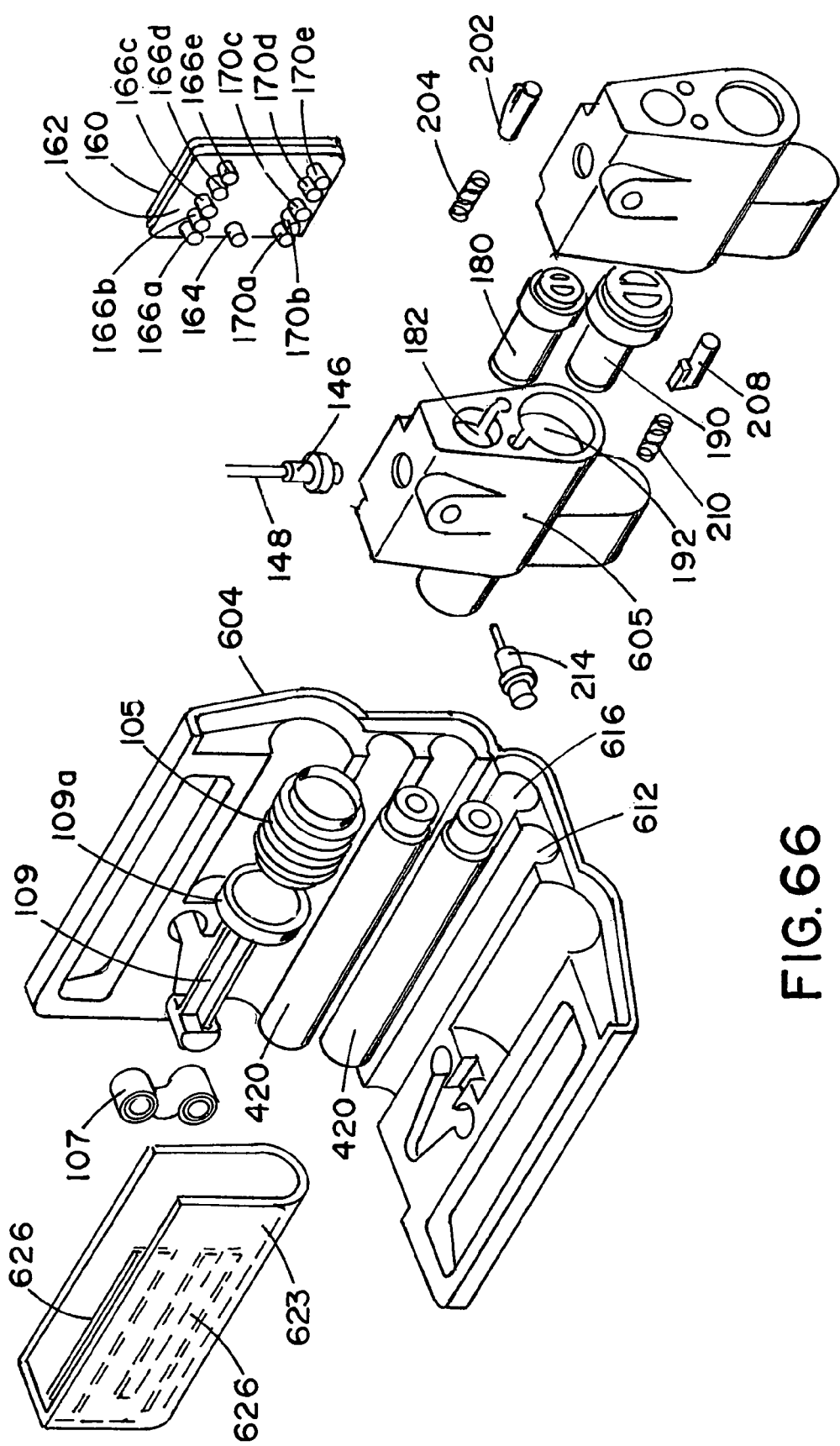
FIG. 66 is a generally perspective, exploded view of the fluid dispensing device shown in FIG. 57.

Turning next to FIGS. 57 through 67, another form of the apparatus of the present invention is there illustrated and generally designated by the numeral 602. This apparatus is similar in some respects to the apparatus shown in FIGS. 37 through 46 and like numerals are used in FIGS. 57 through 67 to identify like components. As best seen in FIG. 57, the primary difference between this latest form of the invention and that shown in FIGS. 37 through 46 concerns the provision of a differently configured reservoir fill means for filling the device reservoir. More particularly, as will presently be described in greater detail, this alternate form of fill means comprises two cartridge type fill vials or containers, rather than one.

As best seen in FIG. 57, the apparatus here comprises an outer housing 604 having first and second portions 604a and 604b respectively. Disposed within outer housing 604a is an inner, expandable housing 105 which is identical in construction and operation to that described in connection with the embodiment of FIGS. 1 through 26.

Also disposed within second portion 604a of the outer housing is the novel stored energy means of the invention for acting upon inner expandable housing 105 in a manner to cause the fluid contained within fluid reservoir 105a thereof to controllably flow outwardly of the housing. In this latest form of the invention, this stored energy means is also identical in construction and operation to that previously described and comprises a constant force spring 107.

With regard to the fill means of this latest form of the invention, which is also carried by first portion 604a of the outer housing, this important fill means functions to fill the reservoir 105a with the fluid to be dispensed. This fill means comprises the previously described septum fill means, which is identical to that previously described and also includes a vial fill means which includes two, rather than the one, fill vial or fill container.

As to the septum fill means, as illustrated in FIG. 57, second housing portion 604b includes a fluid passageway 606 which is in communication with inlet 608 of fluid reservoir 105a. Proximate its lower end 606a, fluid passageway 606 communicates with a cavity 609 formed within the second housing portion. Disposed within cavity 609 is a pierceable septum 610 that comprises a part of the septum fill means of this latest form of the invention. As before, septum 610 is pierceable by the needle of a syringe which contains the medicinal fluid to be dispensed and which can be used in a conventional manner to fill or partially fill reservoir 105a via passageway 606.

First portion 604a of the housing also includes a first chamber 612 for telescopically receiving a first medicament containing fill vial 420 and a second chamber 616 for receiving a second medicament containing vial 420. The fill vials 420 are of identical construction and operation to vial 420 of the earlier described embodiment and the details of their construction will not here be repeated.

A number of beneficial agents can be contained within the two vials 420 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

Forming another very important aspect of the apparatus of this latest form of the invention is a novel flow control means that are carried by second portion 604b of outer housing 604. This flow control means, which is identical in construction and operation to that described in connection with the first embodiment of the invention, functions to precisely control the rate outwardly of fluid flow from reservoir 105a and toward the patient. As before, the flow control means comprises an assembly which includes a base plate, or rate control member 160 and a mating cover member 162 (FIG. 21). As illustrated in FIG. 22, flow rate control member, or base plate 160 is uniquely provided with a plurality of micro rate flow control channels 160a, 160b, 160c, 160d and 160e respectively, which are in communication with the spaced apart micro rate outlet ports of the cover member 162. Flow rate control member, or base plate 160 is also uniquely provided with a plurality of macro rate flow control channels 173a, 173b, 173c, 173d and 173e respectively, which are in communication with the spaced apart macro rate outlet ports of the cover member 162.

Also forming a part of the flow control means of this latest form of the invention is a micro rate selector knob 180 that is carried within a horizontal bore 182 formed in housing portion 604b. Selector knob 180 is of identical construction and operation to the selector knob described in connection with the first embodiment of the invention and is uniquely provided with a plurality of radially extending flow control channels 184a, 184b, 184c, 184d and 184e, each having an inlet port and an outlet port which is in fluid communication with an axially extending passageway 186. Axially extending passageway 186 is, in turn, in fluid communication with administration line 148, which is also of identical construction and operation to that described in connection with the first embodiment of the invention.

Micro selector knob 180, which comprises a part of the selector means of this latest form of the invention, functions to selectively align one of the inlets of the radially extending flow control channels of the selector knob with a selected one of the spaced apart micro rate fluid outlets 166a, 166b, 166c, 166d and 166e of the rate control cover 162 (FIG. 18).

Also forming a part of the flow control means of this latest form of the invention is a macro rate selector knob 190 that is carried within a horizontal bore 192 formed in housing portion 604b. Selector knob 190 is also of identical construction and operation to selector knob 190 as described in connection with the first embodiment of the invention and is uniquely provided with a plurality of radially extending flow control channels 194a, 194b, 194c, 194d and 194e, each having an inlet port and an outlet port which it is in fluid communication with an axially extending passageway 196. Axially extending passageway 196 is, in turn, in fluid communication with administration line 148.

Selector knob 190, which also comprises a part of the selector means of this latest form of the invention, functions to selectively align one of the inlets of the radially extending flow control channels of the macro selector knob with a selected one of the spaced apart macro rate fluid outlets 170a, 170b, 170c, 170d and 170e of the rate control cover 162 (see FIG. 18).

In using the apparatus of this latest form of the invention, following removal of the vial cover 623, which forms a part of the first portion of housing 604 (FIGS. 57 and 67), vials 420 can be inserted into chambers 612 and 616. As previously mentioned, plungers 428 are disposed within vials 420 and are moved by supports 626 of a vial cover 623 (FIGS. 57 and 67) as the vial cover is mated with the apparatus housing. As the plungers 428 move inwardly of their respective vial reservoirs 424, the fluid contained in the reservoirs will be forced through hollow needles 430, passed the umbrella check valves 116 mounted within housing portion 604b, into a stub passageways 630, into passageway 606 and finally into reservoir 105a of the bellows component 105 via inlet 608.

It is also to be understood that, if desired, the reservoir of the bellows component can also be filled by alternate septum filling means of the character previously described. As the reservoir 105a fills with fluid either from the fill vials or from the filling syringe of the alternate septum filling means, any gases trapped within the reservoir will be vented to atmosphere via vent means "V", mounted in portion 604b of the housing.

As the fluid flows into reservoir 105a, the bellows 105d will expand in a manner to exert a rearward pressure on the plunger end portion 109a of pusher member 109 causing it to move rearwardly. As the pusher member moves rearwardly, it will exert forces on spring member 107 causing it to it to expand from its retracted configuration shown in FIG. 57 to its expanded configuration. This rearward movement of pusher member 109 can be viewed through the volume indicator window 142 indicating that the reservoir has changed from an empty configuration to a filled configuration (FIG. 1).

As before selector knobs 180 and 190 are provided with a plurality of circumferentially spaced apart indexing cavities that closely receive the ends of the indexing fingers of outwardly extending locking arms 208, which forms a part of the flow control means of the invention and function to prevent rotation of the selector knobs (see FIGS. 6 and 13). Similarly disabling means of the character previously described can be used to disable the apparatus of this latest form of the invention.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

The invention claimed is:

1. A dispensing apparatus for dispensing fluids to a patient comprising:
   (a) a housing having a fluid reservoir for containing fluid to be dispensed to the patient, said fluid reservoir comprising a bellows structure having an expandable and compressible, accordion-like, annular-shaped sidewall expandable from a first contracted configuration to a second expanded configuration, said housing being provided with an inlet for permitting fluid flow into said fluid reservoir and an outlet for permitting fluid flow from said fluid reservoir;
   (b) pusher means disposed within said housing for movement between a first position and a second position to cause said annular-shaped sidewall to move toward a contracted configuration and to cause said fluid contained within said fluid reservoir to flow toward said outlet of said housing;
   (c) stored energy means disposed within said housing for acting upon said pusher means to cause said pusher means to move toward said second position, said stored energy means comprising a constant force spring;
   (d) fill means carried by said housing for filling said fluid reservoir with the fluid to be dispensed;
   (e) flow control means carried by said housing for controlling fluid flow from said fluid reservoir to the patient, said flow control means comprising:
      (i) first and second selector members rotatably mounted within said housing, each of said first and second selector members having a head portion having a plurality of circumferentially spaced indexing cavities and a body portion having an axially extending passageway and a plurality of radially extending flow control channels, each having an inlet port and an outlet port, said outlet port being in communication with said axially extending passageway; and
      (ii) a flow rate control member mounted within said housing, said flow rate control member having a plurality of elongated fluidic flow control channels in communication with said plurality of radially extending flow control channels formed in said second selector member; and
   (f) dispensing means connected to said housing, said axially extending passageways of said first and second selector members being in communication with said dispensing means.

2. The dispensing apparatus as defined in claim 1 in which said plurality of elongated fluidic flow control channels of said flow rate control member have a depth of approximately 10-100 μm.

3. A dispensing apparatus for dispensing fluids to a patient comprising:
   (a) a housing having a fluid reservoir for containing fluid to be dispensed to the patient, said fluid reservoir comprising a bellows structure having an expandable and compressible, accordion-like, annular-shaped sidewall expandable from a first contracted configuration to a second expanded configuration, said housing being provided with an inlet for permitting fluid flow into said fluid reservoir and an outlet for permitting fluid flow from said fluid reservoir;
   (b) fluid displacement means disposed within said housing for movement between a first position and a second position to cause said fluid contained within said fluid reservoir to flow toward said outlet;
   (c) stored energy means disposed within said housing for acting upon said fluid displacement means to cause said fluid displacement means to move toward said second position, said stored energy means comprising a constant force spring;
   (d) fill means carried by said housing for filling said fluid reservoir with the fluid to be dispensed;
   (e) flow control means carried by said housing for controlling fluid flow from said fluid reservoir to the patient, said flow control means comprising:
      (i) a selector member rotatably mounted within said housing, said selector member having a head portion having a plurality of circumferentially spaced indexing cavities and a body portion having an axially extending passageway and a plurality of radially extending flow control channels, each having an inlet port and an outlet port, said outlet port being in communication with said axially extending passageway; and
      (ii) a flow rate control member mounted within said housing, said flow rate control member being constructed from a medical grade polymer and having a plurality of elongated fluidic flow control channels in communication with said plurality of radially extending flow control channels formed in said selector member, said fluidic flow control channels being made by injection molding techniques; and
   (f) dispensing means connected to said housing and in communication with said plurality of fluid passageways formed in said selector member.

* * * * *